(12) United States Patent
Suzuki et al.

(10) Patent No.: US 7,522,185 B2
(45) Date of Patent: Apr. 21, 2009

(54) TV OBSERVATION SYSTEM FOR ENDOSCOPES INCLUDING A LIGHT SOURCE UNIT HAVING LEDS

(75) Inventors: Takayuki Suzuki, Hachioji (JP); Makoto Tomioka, Hachioji (JP); Yumi Ikeda, Fuchu (JP); Akira Hasegawa, Machida (JP); Mitsujiro Konno, Houya (JP); Shinya Matsumoto, Machida (JP)

(73) Assignee: Olympus Corporation, Tokyo (JP)

( * ) Notice: Subject to any disclaimer, the term of this patent is extended or adjusted under 35 U.S.C. 154(b) by 843 days.

(21) Appl. No.: 10/059,145

(22) Filed: Jan. 31, 2002

(65) Prior Publication Data

US 2002/0089586 A1 Jul. 11, 2002

Related U.S. Application Data

(62) Division of application No. 09/661,474, filed on Sep. 13, 2000, now abandoned, which is a division of application No. 08/805,477, filed on Feb. 25, 1997, now Pat. No. 6,124,883.

(30) Foreign Application Priority Data

Feb. 26, 1996 (JP) ................................. 8-038302
Dec. 18, 1996 (JP) ................................. 8-338385

(51) Int. Cl.
*H04N 7/18* (2006.01)

(52) U.S. Cl. .......................................... 348/70; 348/73
(58) Field of Classification Search ................... 348/68, 348/70, 71, 72, 45, 73; *H04N 7/18*
See application file for complete search history.

(56) References Cited

U.S. PATENT DOCUMENTS

| 4,874,232 | A | 10/1989 | Hasegawa |
| 5,143,435 | A | 9/1992 | Kikuchi |
| 5,155,796 | A | 10/1992 | Oonishi et al. |
| 5,436,655 | A | * | 7/1995 | Hiyama et al. ................. 348/68 |
| 5,577,992 | A | 11/1996 | Chiba et al. |

* cited by examiner

*Primary Examiner*—Young Lee
(74) *Attorney, Agent, or Firm*—Henry J. Daley; Venable LLP

(57) ABSTRACT

A TV observation system for an endoscope including an endoscope and a small-sized light source unit. The endoscope can be structurally separated into an insertion part and a proximal holding part continuously extending from the insertion part. The endoscope can include a light guide arranged from a distal end of the insertion part through the proximal holding part. The proximal holding part can be provided with a light guide joint section where an entrance end face of the light guide is fixed. The small-sized light source unit can be constructed and arranged to be removably connected with the light guide joint section. The small-sized light source unit can include a plurality of small-sized LEDs, a batter configured to power the plurality of LEDs, and a compounding optical system configured to compound light emitted by the plurality of small-sized LEDs.

19 Claims, 13 Drawing Sheets

SUBSTRATE SIDE    AIR SIDE d

FIG. 19A
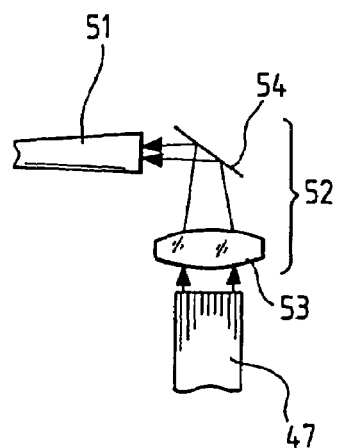
FIG. 19B
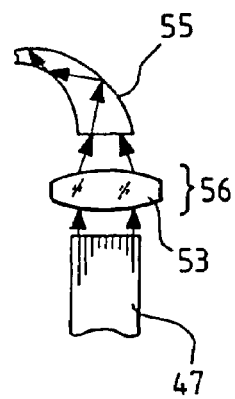
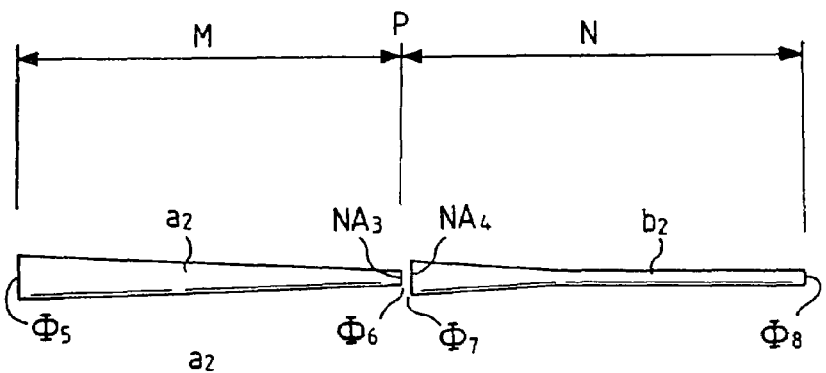
FIG. 20A
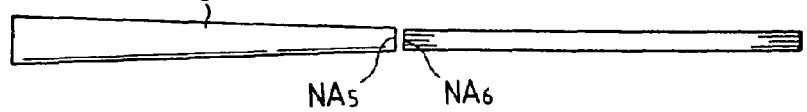
FIG. 20B
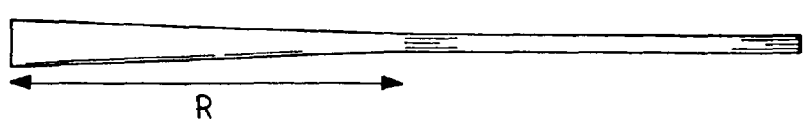
FIG. 20C

TV OBSERVATION SYSTEM FOR ENDOSCOPES INCLUDING A LIGHT SOURCE UNIT HAVING LEDS

CROSS REFERENCE TO RELATED APPLICATIONS

This application is a divisional application of U.S. application Ser. No. 09/661,474, filed Sep. 13, 2000 now abandoned which is a divisional of U.S. application Ser. No. 08/805,477, filed Feb. 25, 1997 now U.S. Pat. No. 6,124,883 the specification and drawings of which are incorporated herein by reference.

BACKGROUND OF THE INVENTION

1. Field of the Invention

This invention relates to a TV observation system for endoscopes in which a battery type power supply and a light source are incorporated in an attachment TV camera.

2. Description of Related Art

In general, an endoscopic observation requires an illumination system, which includes a light source for supplying light to illuminate an object observed; a light guide for transmitting the light from the light source to the distal end of an endoscope; and an illumination lens placed at the distal end of the endoscope to irradiate the object with the light emerging from the light guide. The light source is constructed with a lamp for bringing about intense light, such as a xenon lamp or halogen lamp; a condenser lens for effectively concentrating the light emitted from the lamp on the entrance end face of the light guide; a wavelength-selective filter used for color temperature adjustment; and a stop mechanism for adjusting the amount of light. This light source, however, is equipped with a large-sized power supply section for turning on the lamp and a drive control section for the stop mechanism, and thus is great in volume and heavy in weight as the entire light source device.

In the endoscopic observation, the light source device is placed stationarily, together with a monitor, close to an observer. The endoscope body and the light source device are connected by a light guide cable to introduce the light from the light source device to the distal end of the endoscope. In order to uniformly illuminate the observation field of the endoscope, the distal end of the endoscope is provided with the illumination lens.

Endoscopes are available in fiberscopes and rigid endoscopes for making visual observations and videoscopes for displaying an observation image on a monitor. In recent years, the videoscope has been widely used because it allows many observers to make observations at a time, without undue fatigue. Although it is desirable that even when the fiberscope or rigid endoscope is used, observations are made through the monitor, it becomes necessary in this case to connect an attachment TV camera to the fiberscope or rigid endoscope.

FIG. 1 shows a conventional TV observation system for endoscopes which uses such an attachment TV camera. This system is designed so that an endoscope body 1 coupled through a light guide cable 2 with a light source device 3 is connected to an attachment TV camera 4 coupled through an electric signal cable 5 with a TV processor 6. A monitor 7 for displaying an observation image is connected to the TV processor 6.

The endoscope body 1 has an observing optical system and an illuminating optical system. The illuminating optical system includes a light guide fiber bundle extending from a joint section 8 provided in the endoscope body 1 to the distal end of the endoscope and an illumination lens provided on the exit side of the light guide fiber bundle. The observing optical system, on the other hand, is constructed with an objective lens, an image guide or relay lens for transmitting an image formed by the objective lens, and an eyepiece for observing the transmitted image. The light source device 3 is provided with a lamp and a condenser lens. The light guide cable 2 incorporates a light guide fiber bundle therein so that its entrance end is connected to the light source device 3, and light from the lamp which is concentrated by the condenser lens is received by the entrance end and is transmitted to its exit end connected to the joint section 8. The joint section 8 is provided with an imaging optical system composed of a lens and a conical fiber to connect the light guide of the light guide cable 2 with the light guide of the endoscope body 1. The light emerging from the light guide of the light guide cable 2 is rendered incident in a desired condensing state on the entrance end of the light guide of the endoscope body 1 by the imaging optical,system.

The attachment TV camera 4 is removably mounted to the eyepiece section of the endoscope body 1, and incorporates a photographic lens and an image sensor therein so that the light emerging from the eyepiece of the endoscope body 1 is condensed by the photographic lens to form an object image on the image sensor, by which the object image is converted into an electric signal. The electric signal cable 5 extending from the attachment TV camera 4 is connected to the TV processor 6, which receives the signal from the image sensor and converts it into a signal by which the image can be displayed on the monitor 7.

The light source device 3, the TV processor 6, and the monitor 7 are usually mounted on a single large rack, and when they are moved, a considerably strong force is required to pull them near an observer. Of them, the light source device 3 is largest in size and heaviest in weight.

Thus, the conventional TV observation system for endoscopes mentioned above, although capable of bringing about intense light for illuminating the object, is not easy to move. Furthermore, because the endoscope body 1 is connected by the light guide cable 2 with the light source device 3, the light guide cable 2 constitutes an obstacle to observation, depending on the place where the observation is made. This restricts an observer's behavior and materially reduces his work efficiency.

SUMMARY OF THE INVENTION

It is, therefore, an object of the present invention to provide a TV observation system for endoscopes in which the amount of light sufficient for endoscopic observation can be supplied and the observer's work efficiency is improved.

In order to achieve this object, the TV observation system for endoscopes of the present invention includes a light source emitting light for illuminating an object observed; a power supply for providing the light source with an electric power; an endoscope body; an attachment TV camera removably mounted to the eyepiece section of the endoscope body; and a TV processor for converting an output signal of the attachment TV camera into a signal by which an image can be displayed on display means. The power supply is of a battery type and is incorporated, along with the light source, in the attachment TV camera. It is desirable that the light source is constructed with a combination of small-sized light emitting elements of narrow emission spectrum width.

In the TV observation system for endoscopes according to the present invention, as mentioned above, the light source and the battery type power supply for providing the light source with the electric power are housed in the attachment TV camera, and thus the movement of the system is easy, a long light guide cable connecting the endoscope body and the light source becomes unnecessary, and the observer's work efficiency can be much improved.

Further, since the light source is composed of the small-sized light emitting elements stated above, a large amount of light can be derived with relatively low electric power. Still further, a combination of the light emitting elements of different emission spectra dispenses with the need for the wavelength-selective filter which has been used for color temperature adjustment in the conventional system. Consequently, the light source section becomes more lightweight and compact, and a substantial reduction in manufacturing cost can be intended.

This and other objects as well as the features and advantages of the present invention will become apparent from the following detailed description of the preferred embodiments when taken in conjunction with the accompanying drawings.

BRIEF DESCRIPTION OF TITLE DRAWINGS

Figure 16A:
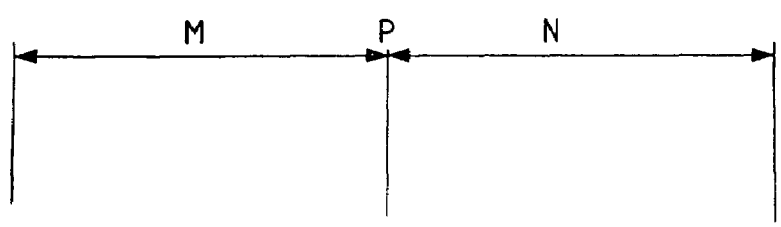
Figure 16B:
Figure 16C:
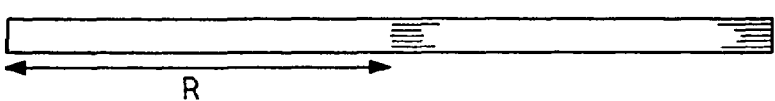
Figure 16D:
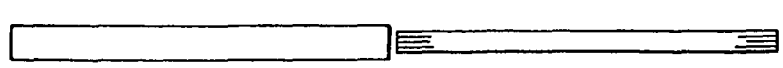
Figure 17:
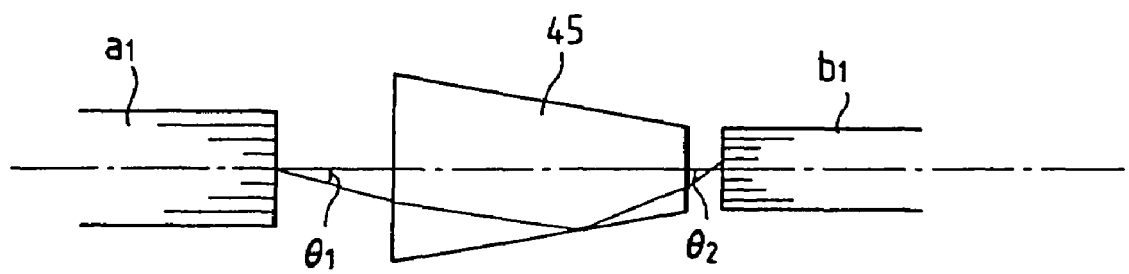
Figure 18:
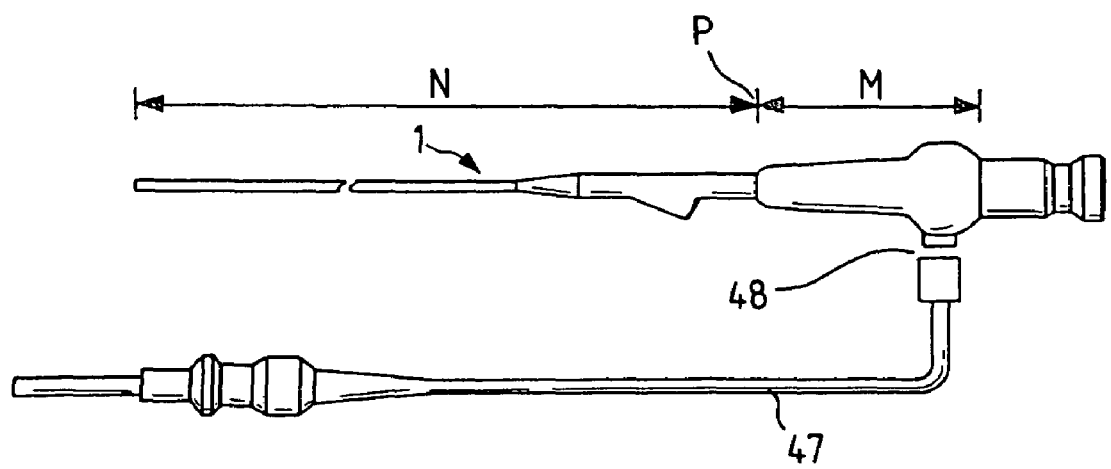
Figure 21A:
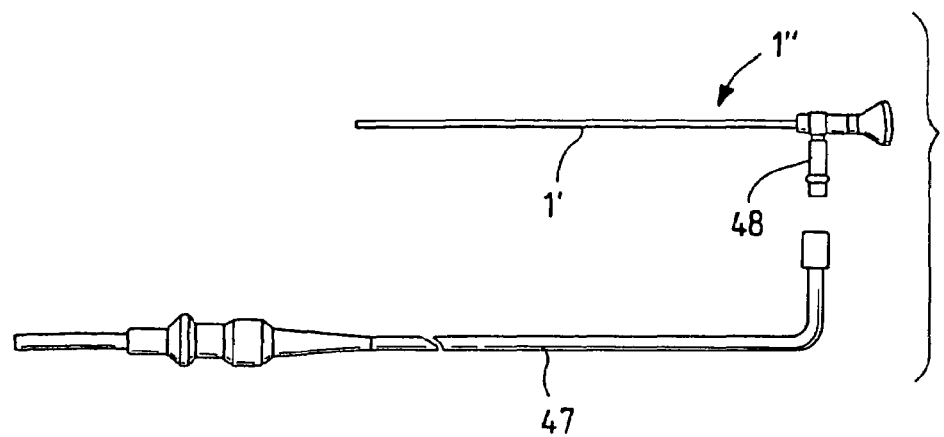
Figure 21B:
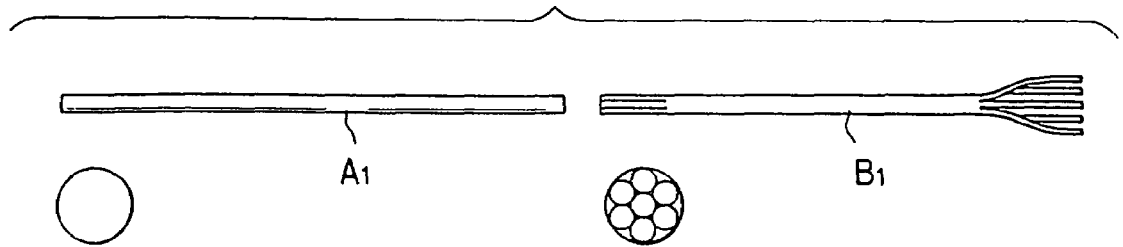
Figure 21C:
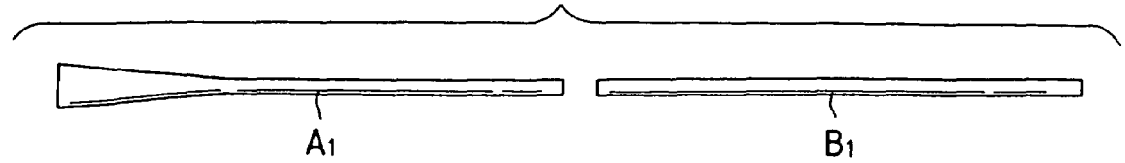
Figure 22:
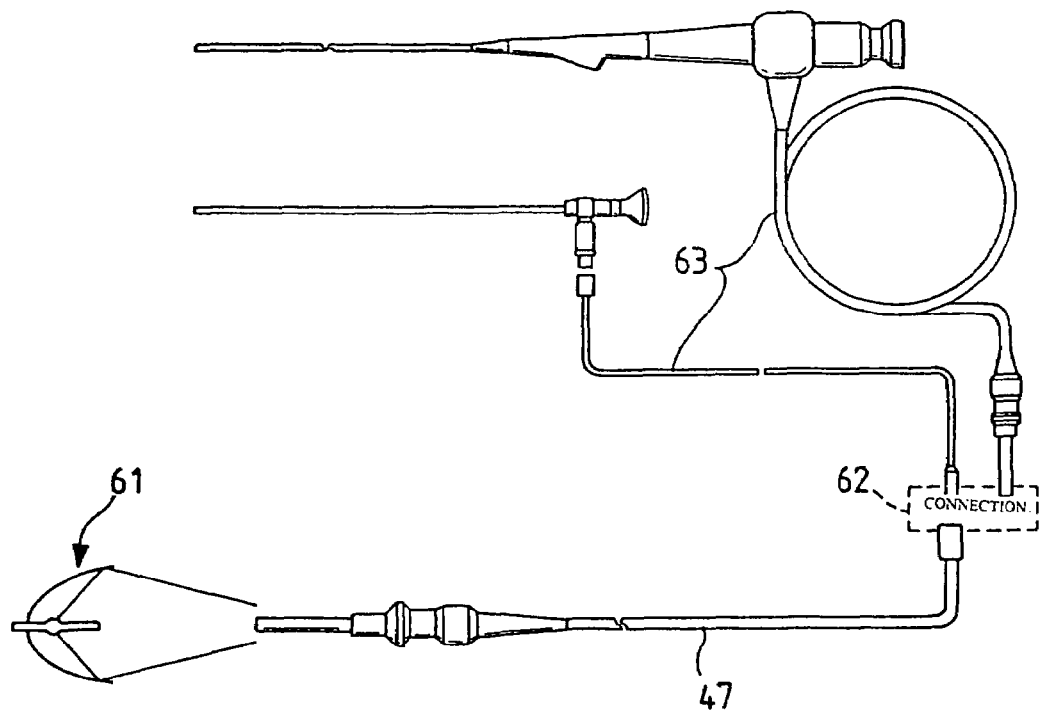
Figure 23A:
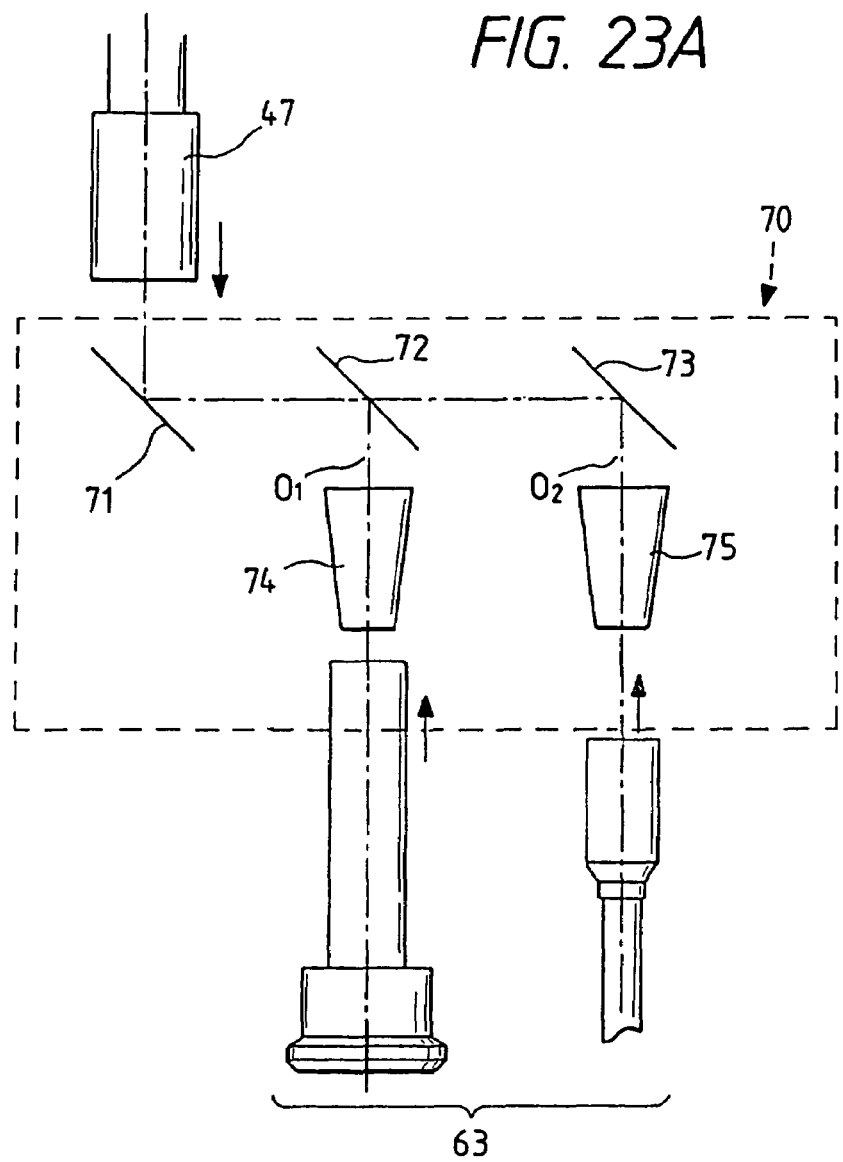
Figure 23B:
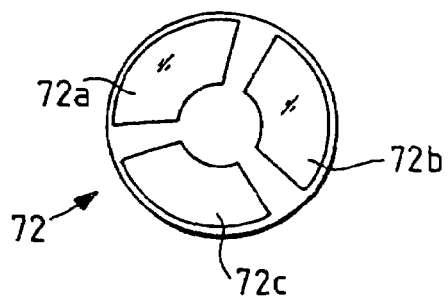
Figure 24:
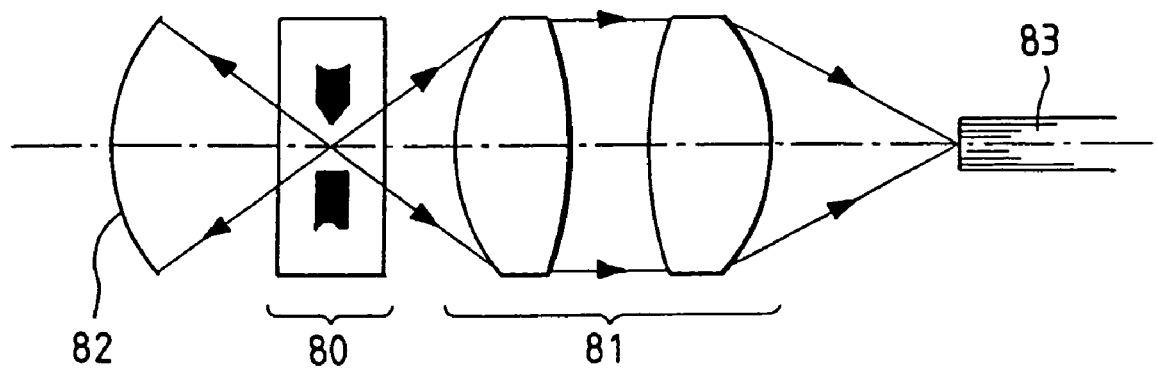
Figure 25A:
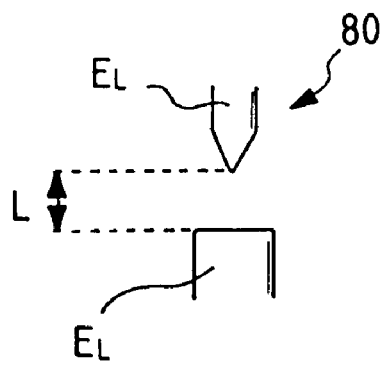
Figure 25B:
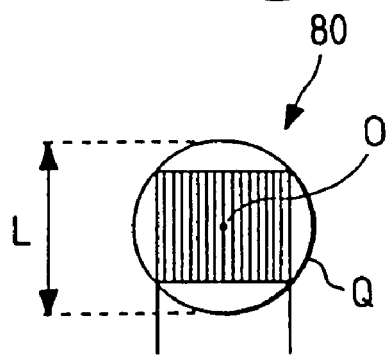

FIGS. 16A, 16B, 16C, and 16D are views showing various constructions relative to the light transmitting section of the illumination system employed in the TV observation system for endoscopes of the fifth embodiment;

FIG. 17 is an enlarged view showing essential parts of the light transmitting section shown in FIG. 16D;

FIG. 18 is a view schematically showing the construction of the endoscope body of the TV observation system for endoscopes according to a sixth embodiment in the present invention;

FIGS. 19A and 19B are views showing arrangements relative to the condensing optical system provided at the connection of the light guide bundle;

FIGS. 20A, 20B, and 20C are views showing various constructions relative to the light transmitting section of the illumination system employed in the TV observation system for endoscopes of the sixth embodiment;

FIG. 21A is a view showing the entire construction of the illumination system used in the TV observation system for endoscopes according to a seventh embodiment;

FIGS. 21B and 21C are views showing examples in the case where the light transmitting section is separated into two located on the light guide side and the endoscope body side in FIG. 21A;

FIG. 22 is a view showing the entire construction of the light transmitting section of the illumination system used in the TV observation system for endoscopes according to an eighth embodiment;

FIG. 23A is a view showing the arrangement of an optical system for connecting light guide cables used in the illumination system of FIG. 22;

FIG. 23B is a front view showing the construction of a path splitting mirror in FIG. 23A;

FIG. 24 is a view showing the arrangement of a light source optical system used in the TV observation system for endoscopes according to a ninth embodiment; and FIGS. 25A and 25B are views showing the dimensions of light-emitting sections of electric discharge and filament types, respectively, used in the light source optical system of FIG. 24.

DETAILED DESCRIPTION OF THE PREFERRED EMBODIMENTS

Figure 1:
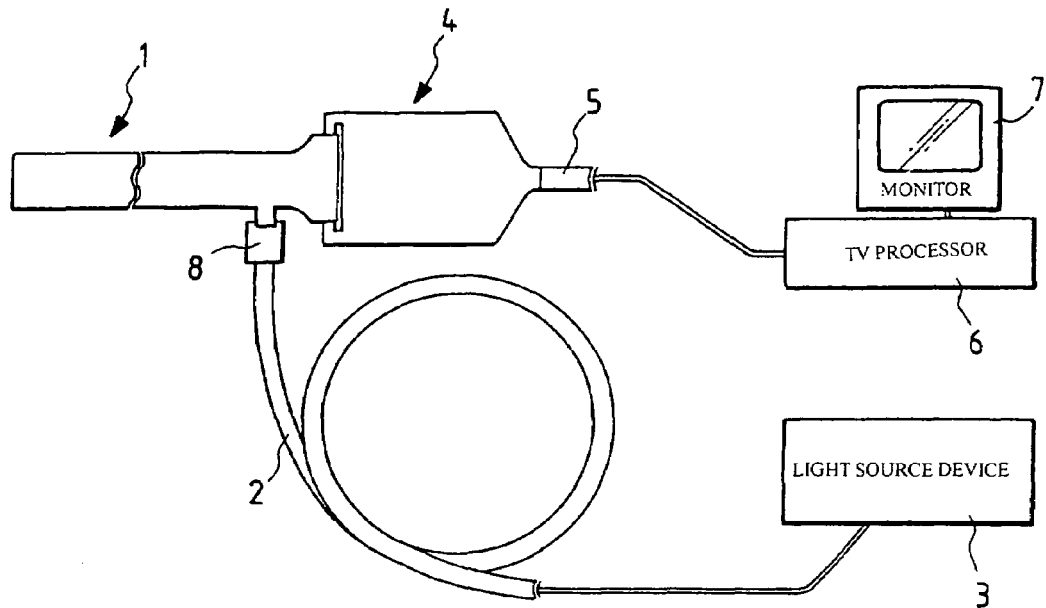
FIG. 1 is a view showing the arrangement of a conventional TV observation system for endoscopes.

In accordance with the embodiments shown in the drawings, the present invention will be explained in detail below. In the drawings, like numerals indicate like members with the conventional example shown in FIG. 1.

First Embodiment

Figure 2:
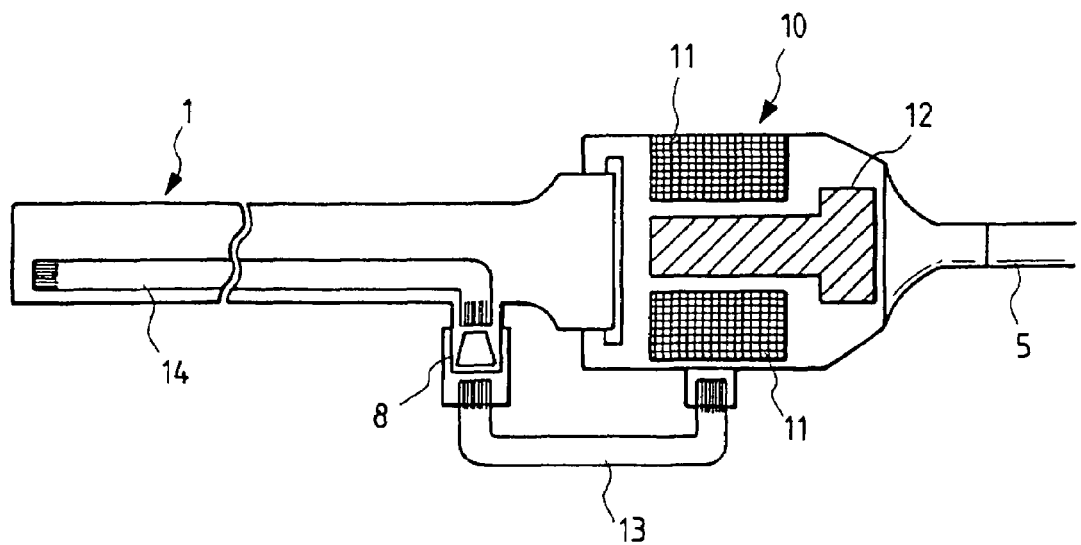
FIG. 2 is a view showing the arrangement of a TV observation system for endoscopes according to a first embodiment in the present invention.

The TV observation system for endoscopes of this embodiment, as shown in FIG. 2, is designed so that an attachment TV camera 10 is connected to the eyepiece section of the endoscope body 1. The endoscope body 1 is the same as that of the conventional system already described in reference to FIG. 1.

The attachment TV camera 10 includes a light source section 11 provided with a charge type power supply and a TV camera functional section 12 having a photographic lens, an image sensor, and a circuit substrate relating to the image sensor which are identical with those used in the conventional system. After an object image caught by the endoscope body 1 is transformed into an electric signal in the TV camera functional section 12, the signal is transmitted to a TV processor, not shown, by an electric signal cable 5 so that the image can be observed through the monitor as in the conventional system. The light source section 11 is equipped with a condensing optical system so that light originating from the light source section 11 is conducted, by a light guide cable 13, through the joint section 8 provided in the endoscope body 1 to a light guide 14. Since the light guide cable 13 is extremely short in the entire length, a loss in the amount of light introduced from the light source section 11 to the endoscope body 1 is minimized, a sufficient amount of light for endoscopic observation is obtained, and the observer's work efficiency is not reduced. Furthermore, the light guide cable 13, for which the light guide cable of the conventional system which is shortened can be used, has interchangeability with respect to the conventional system. In addition, the light guide cable 13 is removably mounted to the joint section 8 and the light source section 11. Hence, for example, where an observer takes much account of obtaining a large amount of light, rather than his work efficiency, it is only necessary to remove the light guide cable 13 from the joint section 8 and the light source section 11 and to connect the conventional stationary light source for a large amount of light by a longer light guide cable with the joint section 8. Also, the power supply provided in the light source section 11 is available in an interchange type in addition to the charge type.

In the TV observation system for endoscopes of the first embodiment, as mentioned above, the attachment TV camera 10 is connected through the electric signal cable 5 with the TV processor, and thus the entire system cannot necessarily be moved with freedom. However, the light source section 11 provided with the power supply is incorporated in the attachment TV camera 10, thus doing away with the need for a large power supply placed on the outside thereof. Consequently, by merely pulling a bench on which the TV processor and the monitor which are relatively light in weight are mounted, together with the endoscope body 1 and the attachment TV camera 10 connected thereto, the entire system can be moved with comparative ease.

In the system of the first embodiment, the light source section 11 is constructed with a combination of small-sized light emitting elements of narrow emission spectrum width. For example, where elements, such as LEDs, emitting light of wavelengths of red, green, and blue colors are used to constitute the light source section 11, the load currents of the elements are adjusted, and thereby the amounts of emission light of the elements are set in a desired ratio for color temperature adjustment. Alternatively, red, green, and blue light are emitted in accordance with time difference, and thereby a light source of field sequential system can be attained. Also, such light emitting elements may be arranged in an array.

Figure 3A:
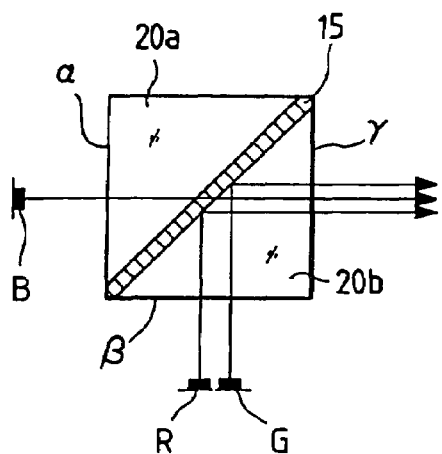
FIG. 3A is a view showing one construction example of a condensing optical system of a light source section used in the TV observation system for endoscopes of the first embodiment.
Figure 3B:
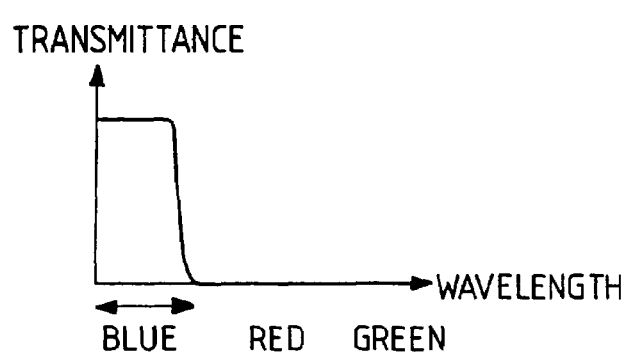
FIG. 3B is a graph showing spectral characteristics of a coating film applied to the condensing optical system of FIG. 3A.

Next, a description will be given of examples of the condensing optical systems, each of which is mounted in the light source section 11 provided with these light emitting elements. FIG. 3A shows the condensing optical system of the light source section 11 which uses a prism assembly in which two right-angled prisms are cemented and shaped into a cubic form. A band-pass coat is applied to the interface where two prisms 20a and 20b are cemented. The spectral characteristics of a coating film 15 of this, as shown in FIG. 3B, are such that the blue light is transmitted and the red and green light are reflected. A blue light emitting element B is disposed opposite to a surface $\alpha$ of the prism 20a, and a red light emitting element R and a green light emitting element G are placed opposite to a surface $\beta$ of the prism 20b. Light from the blue light emitting element B is incident on the surface $\alpha$ of the prism 20a, and after being transmitted through the coating film 15, emerges from a surface $\tau$ of the prism 20b. On the other hand, light from the red light emitting element R and the green light emitting element G is incident on the surface $\beta$ of the prism 20b, and after being reflected by the coating film 15, emerges from the surface $\tau$ of the prism 20b. At this time, light of three colors of blue, red, and green is compounded by the prism 20b into white light when leaving the prism 20b.

Also, although the transmission wavelength of the coating film 15 described here corresponds to the blue light and the reflection wavelength thereof to each of the red and green light, the wavelength regions of transmission and reflection can be arbitrarily set when necessary.

Figure 4:
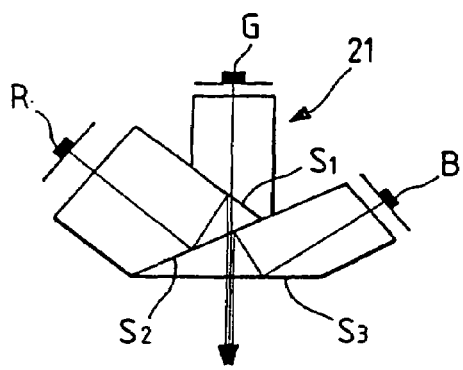
FIG. 4 is a view showing another construction example of the condensing optical system of the light source section used in the TV observation system for endoscopes of the first embodiment.

FIG. 4 illustrates the condensing optical system of the light source section 11 which uses the same prism as a three-color separation prism employed in a common TV camera. As shown in the figure, a prism 21 has three interfaces S1, S2, and S3. The red, green, and blue light emitting elements R, G, and B are arranged opposite to the corresponding entrance surfaces of the prism 21. The interface S1 is constructed with a diachronic mirror so that only the red light is reflected and the other color light is transmitted. In contrast to this, each of the interfaces S2 and S3 constitutes a total reflection surface. In this way, light from the green light emitting element G emerges from the prism 21 without reflection by any interface. Light from the red light emitting element R, after being totally reflected by the interface S2, is reflected by the interface S1 reflecting the red light only, and is transmitted through the interface S2 to emerge from the prism 21. Light from the blue light emitting element B is totally reflected by the interface S3 and then is further totally reflected by the interface S2 to emerge from the prism 21. In this case, if careful consideration is not taken as to the spectral characteristics of the light emitted from the red light emitting element R and the green light emitting element G and the spectral reflectance characteristic of the interface S1, a loss of the amount of light will be caused. Specifically, for example, if the light from the red light emitting element R includes wavelength components which are not reflected by the interface S1, these wavelength components will be transmitted through the interface S1 and lost, thus causing a corresponding loss of the amount of light.

Hence, where the condensing optical system of the light source section 11 is constructed with the prism 21, the spectral characteristics of the light emitted from the light emitting elements are reconciled with the spectral reflectance characteristic of the interface S1, and thereby three-color light emerging from the prism 21 can be produced as mixed light without any loss.

Figure 5:
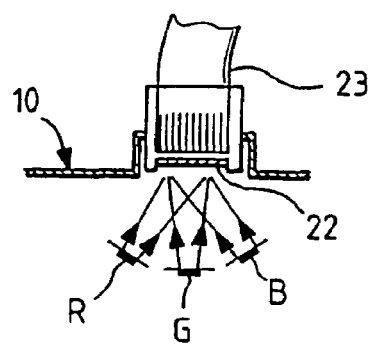
FIG. 5 is a view showing still another construction example of the condensing optical system of the light source section used in the TV observation system for endoscopes of the first embodiment.

FIG. 5 shows the condensing optical system of the light source section 11 which uses a very thin planar plate 22, such as frosted glass, possessing the function of diffusing light. This condensing optical system is such that light from the light emitting elements is radiated directly to a light guide 23 of the light guide cable 13 and thereby is mixed. Where the condensing optical system constructed with the planar plate 22 is provided in the light source section 11, the light emitting elements R, B, and G are arranged so that the light from each of them can be effectively incident on the planar plate 22. In this case, if an arrangement is made so that the end face of the light guide 23 is located immediately behind the planar plate 22, the loss of the amount of light can be prevented. As such, when the planar plate 22 is placed as protection glass for the end face of the light guide 23 of the light guide cable 13, a better effect is brought about. Specifically, since the planar plate 22 having such a diffusing function scatters the incident light in all directions, the light from the three light emitting elements is almost uniformly mixed on the side of emergence of the light from the plate 22, regardless of the direction of incidence of the light on the plate 22. This mixed light is received by the light guide 23. In this case, the emergent light from the planar plate 22 is scattered in all directions, and thus if the distance between the plate 22 and the light guide 23 is extremely long, the emergent light from the plate 22 will spread far and wide and light missing the light guide 23 will increase. It is thus desirable that the plate 22 is placed as close to the light guide 23 as possible. Also, the planar plate 22 may be designed so that a fine groove pattern is ruled on the surface of the plate 22 by a technique, such as etching, to have the diffusing function making use of the diffraction effect of light. When the planar plate 22 is used as mentioned above, the number of degrees of layout freedom of each light emitting element is increased, and the light source section 11 can be compactly designed.

Figure 6:
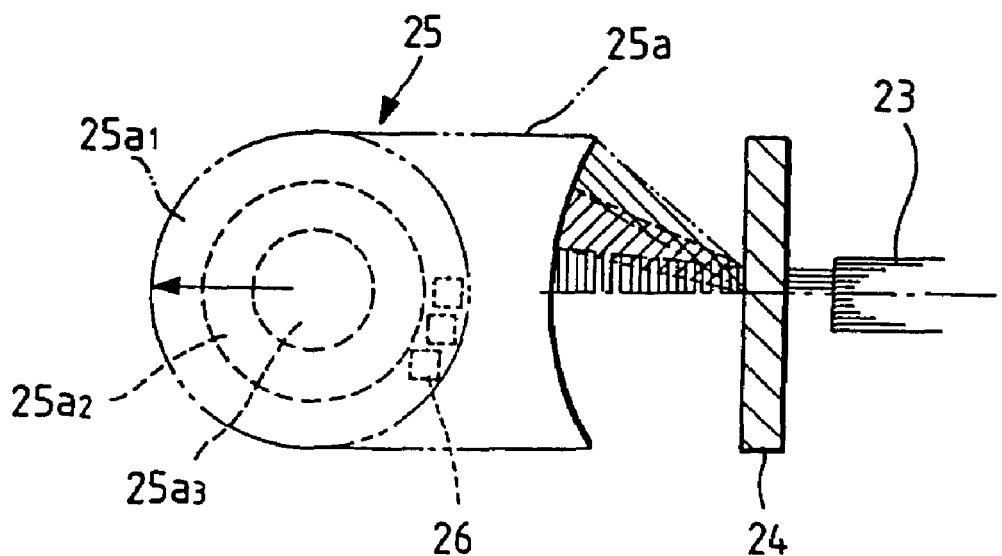
FIG. 6 is a view showing a further construction example of the condensing optical system of the light source section used in the TV observation system for endoscopes of the first embodiment.

FIG. 6 shows the condensing optical system of the light source section 11 which uses a diffractive optics element (hereinafter referred to as "DOE") 24. A light source 25 provided in the light source section 11 is such that a plurality of light emitting elements 26 of different emission spectra (the red, green, and blue light emitting elements R, G, and B) are arranged in an array of concentric circles on a nearly spherical substrate 25a. Light emitted from the light source 25 is incident on the DOE 24 with its diffraction face directed toward the light source 25.

Figure 7A:
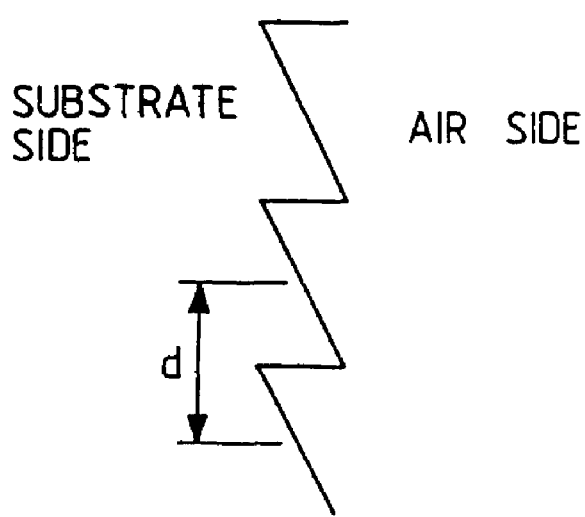
FIGS. 7A and 7B are views showing sections of diffractive optics elements used in the condensing optical system of FIG. 6.
Figure 7B:
Figure 8A:
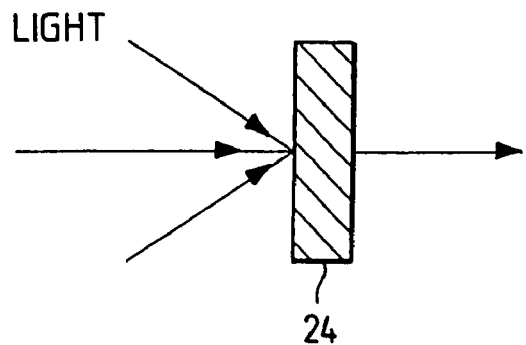
FIGS. 8A and 8B are views for explaining the function of the diffractive optics element.

The DOE is an optical element in which the surface of a base plate made of glass or plastic, as shown in FIG. 7A, assumes the shape of saw-toothed cross section. In practice, it is difficult to shape the surface into a perfect saw-toothed form, and thus, as shown in FIG. 7B, the diffraction face is configured approximately in such a way that its inclined sides are stepped by etching. It is possible that such diffractive optics elements are provided with various functions by changing a pitch d at will. The DOE 24 used in the first embodiment, as illustrated in FIG. 8A, has the function of mixing incident light.

Figure 8B:
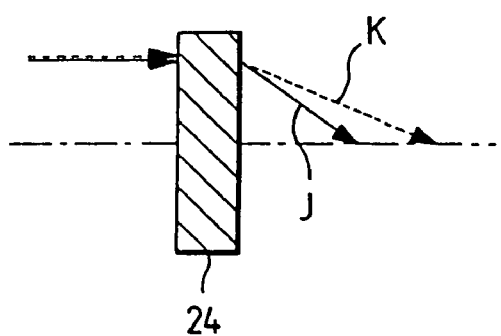

A ray of light incident on a common optical lens is refracted, following Snell's law, while the refraction of that incident on the DOE obeys the law of diffraction. Specifically, as depicted in FIG. 8B, a ray J of long wavelength is larger in angle of refraction than a ray K of shorter wavelength. For this reason, the light source 25 used in the first embodiment is designed so that the light emitting elements (LEDs) 26 separately emitting the light of red, green, and blue colors are arranged in the concentric circular array on the nearly spherical substrate 25a. In this case, the red light emitting elements R emitting the red light of long wavelength is placed on an outer annulation 25a1 of the substrate 25a where the ray has the largest angle of incidence on the DOE 24, whereas the green and blue light emitting elements G and B emitting the green and blue light of shorter wavelengths are arranged on middle and inner annulations 25a2 and 25a3, respectively, of the substrate 25a where the rays have smaller angles of incidence on the DOE 24. Thus, in view of chromatic aberration produced by the DOE 24, the light emitting elements are arranged so that this aberration is corrected, and hence three color rays can be uniformly mixed. Also, since the DOE 24 is constructed so that the diffraction face can easily be configured on an extremely thin planar glass base plate, it is possible to design the light source optical system very compactly.

Figure 9:
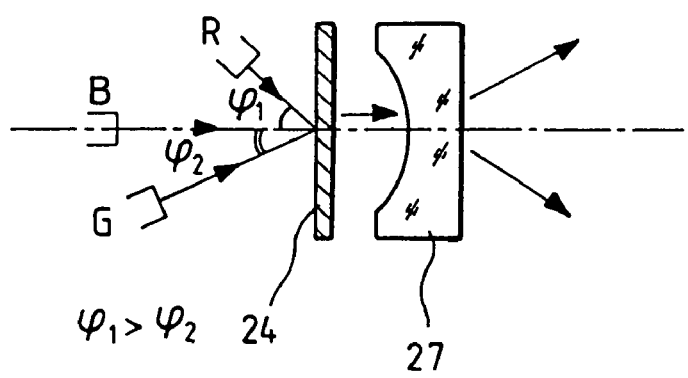
FIG. 9 is a view showing a still further construction example of the condensing optical system of the light source section used in the TV observation system for endoscopes of the first embodiment.

FIG. 9 illustrates an example where the light source optical system including the DOE 24 is placed at the distal end of the endoscope. Since the distal end of the endoscope is already equipped with an illuminating optical system, followed by an objective optical system, an electronic pickup section, and forceps, in a tiny space, the placement of the light source optical system, in addition to these, causes oversizing in diameter of the distal end of the endoscope. Thus, in the first embodiment, the DOE 24 with the diffraction face configured on the extremely thin glass base plate is disposed, immediately before an illuminating optical system 27, as the light source optical system, which is made to coexist together in a space originally occupied by the illuminating optical system. This makes it possible to place the light source at the distal end of the endoscope with a conventional tiny diameter. In this case, the red, green, and blue light emitting elements R, G, and B emitting the red, green, and blue light are arranged in such a way that their positions are shifted with respect to one another in the direction of the optical axis of the illuminating optical system 27 and the light source optical system. Such an arrangement is very effective for making free use of a highly limited, tiny space. In order to correct for chromatic aberration produced by the DOE 24, the arrangement is such that the angle of inclination of the light emitting element with the DOE 24 increases with increasing wavelength of the light emitting element. Specifically, an angle of inclination ø1 of the red light emitting element R is made larger than an angle of inclination ø2 of the green light emitting element G.

Since light passing through the DOE is changed to a light beam nearly parallel with the optical axis and is made divergent by the illuminating optical system 27 to radiate toward an object, a bright image can be secured in the range from the center of an observation field to the periphery thereof. The DOE 24 can be provided with the function of making light divergent and thus, if a DOE of convergence type is used as the illuminating optical system, it becomes possible that an arrangement ranging from the light source to the illuminating optical system is made compact. Also, the condensing optical system explained in reference to FIGS. 3A-9 possesses the function of compounding light from the light emitting elements R, B, and G as well as condensing light, and thus may also be called a compounding optical system.

For the light source section 11, a light emitting element emitting white light or a small-sized lamp may be used, and in this case, by adjusting the amount of emission light of the light source, a desired amount of light can be derived. Since, however, a xenon lamp, for example, has emission spectra over a wide wavelength region containing infrared and ultraviolet radiation in addition to light (visible) used for observations, unwanted light for observations is produced, and power consumption is increased accordingly, which is of no use. As such, in view of the working efficiency of the power, it is desirable to use a light source with narrow emission spectrum width which produces only rays required.

It is also possible that the TV observation system for endoscopes of the first embodiment is constructed so that the light source section 11 provided with the power supply is unitized and can be removably mounted to the attached TV camera 10. In this case, a plurality of attachment TV cameras can be used interchangeably with respect to the light source section 11. Where only the function of the attachment TV camera is utilized, the light source section 11 may be removed. Moreover, when the light source section 11 is unitized, the light source section 11 is removed and is incorporated in a stationary light source for a large amount of light to be used as its auxiliary light source.

Since, as mentioned above, the light source section 11, which is unitized, can be removed from the attachment TV camera 10 when necessary, and is used as the auxiliary light source, the system can have exceptional versatility. Where the light source section 11 is incorporated in the stationary light source for a large amount of light, power failure is prevented in such a way that the power supply provided in the light source section 11 is always charged. Thus, a stable endoscopic observation becomes possible.

Second Embodiment

Figure 10:
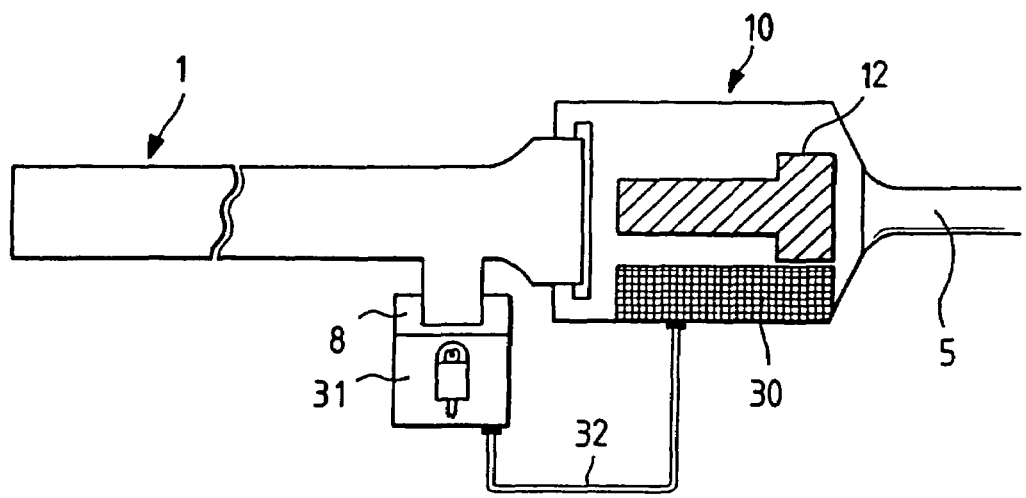
FIG. 10 is a view showing the arrangement of the TV observation system for endoscopes according to a second embodiment in the present invention.

In the TV observation system for endoscopes of this embodiment, as shown in FIG. 10, a power supply 30 is constructed independently of a light source section 31. The power supply 30 is incorporated in the attachment TV camera 10, while the light source section 31 is connected to the joint section 8 of the endoscope body 1. The light source section 31 is provided with the condensing optical system shown in any one of FIGS. 3A, 4-6, and 9. Electric power from the power supply 30 is supplied through a power supply cable 32 to the light source section 31. Other constructions are the same as in the first embodiment.

With this system, since the light guide cable becomes unnecessary and light emitted from the light source section 31 reaches the endoscope body 1 without loss of the amount of light, the illuminance of illumination light of the endoscope can be completely prevented from being reduced. In the conventional system in which a relatively long light guide cable has been used, if a load, such as extreme bending, is applied to the light guide cable, internal fibers will be broken off and light ceases to be transmitted. In this way, when the conventional system is used for a long period of time, it is imperative that the amount of transmitted light be reduced, but according to the system of the second embodiment, such a problem is not produced.

Third Embodiment

Figure 11:
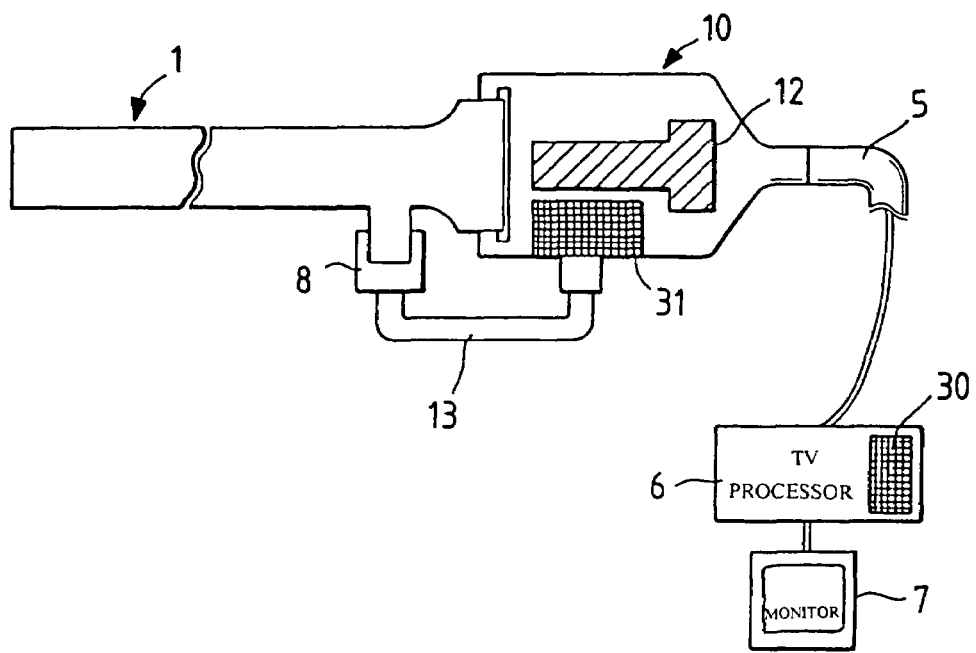
FIG. 11 is a view showing the arrangement of the TV observation system for endoscopes according to a third embodiment in the present invention.

The TV observation system for endoscopes of this embodiment, as shown in FIG. 11, is also constructed so that the power supply 30 is placed independently of the light source section 31. The light source section 31 is provided in the attachment TV camera 10 and has the condensing optical system shown in any one of FIGS. 3A, 4-6, and 9. The power supply 30, on the other hand, is housed in the TV processor 6 for imaging the electric signal from the attachment TV camera 10. The power supply cord is encased in the electric signal cable 5 connecting the attachment TV camera 10 and the TV processor 6, and thereby the power supply 30 is connected with the light source section 31. The light source section 31 and the joint section 8 of the endoscope body 1, as in the first embodiment, are connected by the very short light guide cable 13.

In the system of the third embodiment constructed as mentioned above, the power supply 30 which is relatively large and heavy is incorporated in the TV processor 6, and hence the attachment TV camera 10 is characteristic of a lightweight and compact design.

Fourth Embodiment

Figure 12:
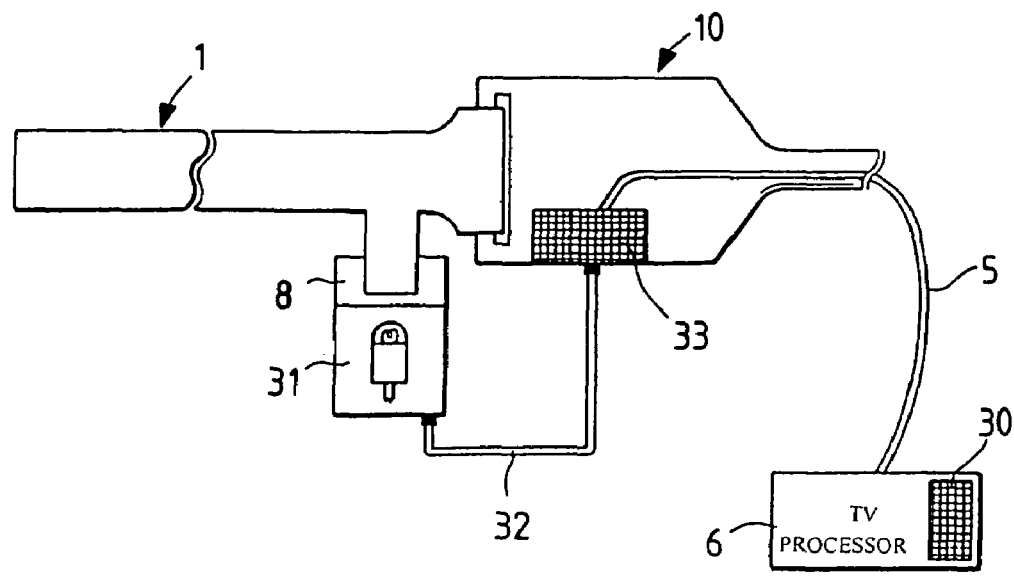
FIG. 12 is a view showing the arrangement of the TV observation system for endoscopes according to a fourth embodiment in the present invention.

The TV observation system for endoscopes of this embodiment, as shown in FIG. 12, is also constructed so that the power supply 30 is placed independently of the light source section 31. The power supply 30, as in the third embodiment, is provided in the TV processor 6, while the light source section 31 has the condensing optical system shown in any one of FIGS. 3A, 4-6, and 9 and is connected to the joint section 8 of the endoscope body 1. The attachment TV camera 10 is provided with a power supply joint section 33, which is connected by the power supply cable encased in the electric signal cable 5 with the power supply 30 of the TV processor 6. The light source section 31 is connected through the power supply cable 32 with the power supply joint section 33 to receive the supply of the electric power.

Thus, in the system of the fourth embodiment also, the use of the light guide cable is not required and the light from the light source section 31 is transmitted without any loss. Furthermore, the attachment TV camera 10 can be used without practically changing its conventional design. This is advantageous to cost.

Fifth Embodiment

In general, an illumination system for endoscopes for supplying light is incorporated in an endoscopic observation apparatus for observing the interiors of a human body and of an object covered by a partition wall like a pipe to which incoming light is inaccessible. The illumination system for endoscopes comprises a light source for supplying light to illuminate an object observed; a light transmitting section for transmitting the light from the light source to the distal end of the endoscope; and an illumination lens system placed opposite to the object at the distal end of the endoscope, for sufficiently illuminating an observation field from the center to the periphery thereof. In the endoscopic observation, the light source device is placed stationarily, together with a monitor, close to an observer, and a light guide cable extending from the endoscope body or a light guide cable independent of the endoscope body is used to connect the endoscope body with the light source device, thereby introducing the light to the distal end of the endoscope.

Endoscopes are available in two types, a soft endoscope in which a portion inserted in an observation part is flexible and a rigid endoscope which is non-flexible. In either of them, it is intended that the diameter of the portion inserted in the observation part is rendered smaller in order to bring about the improvement of insertion in the observation part and a reduction of pain on a patient. When the diameter is thus rendered smaller, a space which can be occupied by the illumination system will be highly limited. In order to meet this problem, it is necessary to materially reduce the rate of space occupied by the light guide, compared with the case of the conventional endoscope of this type. However, this obstructs the introduction of the amount of light sufficient for illuminating the object from the light source to the distal end of the endoscope, and thus it becomes difficult to richly illuminate the observation field. Moreover, it also becomes difficult to place the illumination lens system because of a smaller diameter of the distal end of the endoscope.

In order to repair these defects, a technique is known that the exit end of the light guide in the periphery of the distal end of the endoscope is shaped into an annular form to thereby ensure the distribution of illumination light without using the illumination lens system. With only this technique, however, the distribution of light sufficient for observations cannot be obtained. This is because an angular aperture ($\omega$) of the light guide used in the endoscope is as relatively small as 20-40°, whereas an observation field angle ($2\theta$) is as large as 80-140°. In the observation of the endoscope, it is common practice that a particular observation part is first determined in view of the entire observation range, and then the distal end of the endoscope is rendered close to the particular observation part to make minute observations. In this case, however, when the entire observation range is viewed, shortages in the amount and distribution of illumination light are particularly pronounced.

In view of the above problems, the fifth embodiment provides the TV observation system for endoscopes in which the distal end and insertion part of the endoscope can be constructed with small diameters and the illuminance of the observation field can be completely secured.

Figure 13:
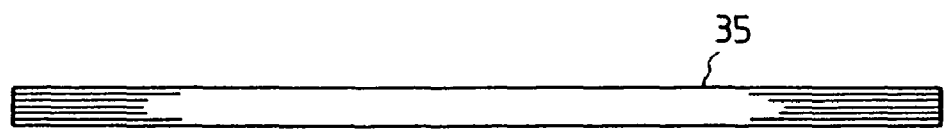
FIG. 13 is a view showing the construction of a light transmitting section of an illumination system used in the conventional TV observation system for endoscopes.

The light transmitting section of the illumination system used in the conventional TV observation system for endoscopes, as illustrated in FIG. 13, uses a light guide fiber bundle (hereinafter referred to as "LG bundle") 35 in which a plurality of fiber elements are bundled to cement and process their ends. When the diameter of the distal end of the endoscope is rendered small and the number of fiber elements constituting the LG bundle placed at the distal end of the endoscope is decreased, the number of fiber elements of the LG bundle provided in an operating section of the endoscope and the light guide cable which do not structurally require the small diameters will also be decreased accordingly.

As such, in the illumination system used in the fifth embodiment, the light transmitting section is divided into two parts at an arbitrary position between the entrance end on the light source side and the exit end at the distal end of the endoscope so that an optimum light transmitter is provided in each part. In this way, the shortages of the amount and distribution of illumination light caused by a diminution in diameter of the endoscope are eliminated.

Figure 14A:
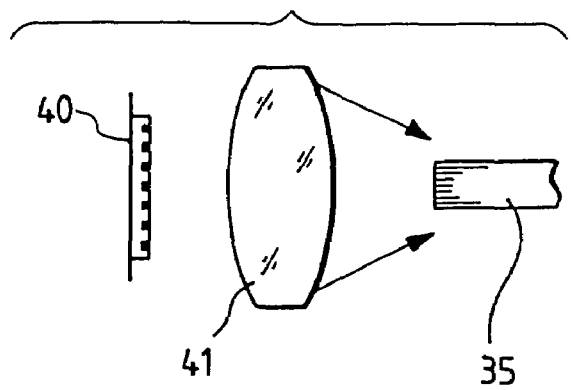
FIG. 14A is a view showing an arrangement relative to the light source of a light guide bundle used in the conventional endoscope.
Figure 14B:
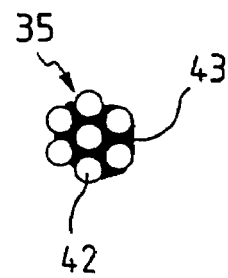
FIG. 14B is a sectional view of the light guide bundle shown in FIG. 14A.

Here, attention is directed to the entrance end which receives light from the light source. In general, even though light emitted from a light emitter of certain size, as shown in FIG. 14A, composed of a light source 40 like the LED is collected through a condensing optical system 41 at the entrance end of the LG bundle 35, the light will be spread without meeting in a focus. Hence, in order to capture light most copiously, it is desirable to make the area of the entrance end of the LG bundle 35 as large as possible. Further, as shown in FIG. 14B, the LG bundle 35 is such that a plurality of fiber elements 42 is secured with an adhesive 43 and thus, at the entrance end, the adhesive 43 is charged without clearance between the fiber elements. Part of the light incident on the entrance end, when striking the adhesive, is reflected or absorbed into the adhesive and is not transmitted. Thus, a loss in the amount of light is caused in accordance with the rate of the area of the entrance end occupied by the adhesive. In order to extenuate this loss, it is desirable that the portion of the adhesive which is opaque to the light is diminished from the entrance end as far as possible.

Figure 15:
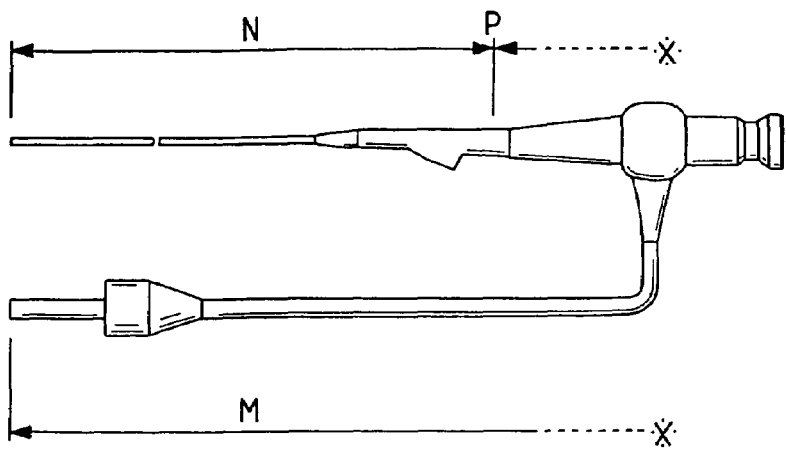
FIG. 15 is a view schematically showing the construction of the endoscope body of the TV observation system for endoscopes according to a fifth embodiment in the present invention.

In view of these respects, the fifth embodiment employs a single fiber, instead of the LG bundle 35. In the endoscope body shown in FIG. 15, one light transmitting part between the entrance end on the light source side and an arbitrary point P is taken as M and another light transmitting part between the arbitrary point P and the exit end at the distal end of the endoscope is taken as N. The light transmitting section shown in FIG. 16A uses a single fiber in place of the conventional LG bundle 35. The light transmitting part M is designed so that a sectional area $\Phi n$ parallel to the entrance end decreases in accordance with a linear or nonlinear rule in going from the entrance end to the arbitrary point P, while the light transmitting part N is such that a sectional area $\Phi n'$ parallel to the exit end is identically equal between the arbitrary point P and the exit end. In the light transmitting part M, an area $\Phi 1$ of the entrance end is largest. Thus, the amount of light caught at the entrance end is remarkably increased as compared with that of the conventional LG bundle. The light incident on the fiber elements constituting the LG bundle 35, when transmitted toward the distal end of the endoscope, is repeatedly reflected between fiber sides, and the loss of the amount of light is caused accordingly. However, when the single fiber is used as in the fifth embodiment, the number of reflections of light between the fiber sides is considerably reduced and the loss of the amount of light can be suppressed.

Furthermore, the light transmitting section used in the fifth embodiment, as described in reference to FIG. 16A, is such that the sectional area of the single fiber is reduced progressively in going from the entrance end to the arbitrary point P, and the single fiber is shaped into a practical taper form. Consequently, the light incident on the entrance end is totally reflected repeatedly in the region of the light transmitting part M, so that an angle made with the optical axis of the single fiber is larger than that of the case of incidence on the entrance end, and the distribution of light emerging from the exit end can be improved.

In the light transmitting part N, on the other hand, the single fiber is shaped to have an extremely small diameter in accordance with a tendency to the smaller diameter of the distal end of the endoscope. By doing so, the single fiber is provided with flexibility and thus can be used for the light transmitting section of the endoscope which requires the distal end to be flexed.

Calling $\Phi 2$ the area of the exit end, it is necessary that the single fiber satisfies a condition:

$$\Phi 1 > \Phi 2 \tag{1}$$

In a medical endoscope for observing parts with many curves, such as digestive organs and bronchi, in the human body as well as in an industrial endoscope for observing the interiors of complicated fine pipes, at least a portion of the endoscope inserted in the observation part must have sufficient flexibility. A comparison of the LG bundle with the single fiber shows that for the transmission efficiency of light, the single fiber is much more advantageous, while for flexibility, the LG bundle is much more excellent. Thus, it is one of the aims of the fifth embodiment that the LG bundle having excellent flexibility is used for the light transmitting part provided in at least a portion of the endoscope requiring sufficient flexibility to markedly improve the ability to transmit light as compared with the conventional system.

To achieve this aim, the light transmitting section shown in FIG. 16B is provided. This light transmitting section is divided into two parts, at the arbitrary point P, the light transmitting part M which requires very little flexibility and the light transmitting part N which requires sufficient flexibility as in at least a portion inserted in the observation part. In other words, the light transmitting part M is provided with a rigid portion having non-flexibility, while the light transmitting part N is provided with a soft portion having flexibility. In the region of the light transmitting part M, the LG bundle is heated and thereby the fiber elements are fused into a single fiber form as a fused part R. By doing so, the incidence efficiency of light at the entrance end, as well as the transmission efficiency of light in the region of the light transmitting part M, can be improved. In the region of the light transmitting part N, on the other hand, the LG bundle is used to provide flexibility by priority and thus can be favorably inserted in the observation part assuming a complicated curved shape. Moreover, it becomes possible that the observation part is copiously illuminated by the endoscope. Also, similar to the light transmitting section shown in FIG. 16A, if the area of the entrance end is made larger than that of the exit end and the fused part R between the entrance end and the arbitrary point P is shaped into a practical taper form, the light transmitting section of the TV observation system for endoscopes can be realized which has a more bright, wide range of distribution of light.

In this case, if, in FIG. 16B, the fused part R in the region of the light transmitting part M is regarded as a single fiber element, the following relation is established between the number of fiber elements n1 of the light transmitting part M and the number of fiber elements n2 of the light transmitting part N:

$$n1 < n2 \quad (2)$$

The light transmitting section shown in FIG. 16C is such that light transmitters which are respectively composed of the light transmitting parts M and N shown in FIG. 16B are constructed independently of each other. In the light transmitting section of FIG. 16C, the light transmitting part M is configured as a single fiber rod lens, while the light transmitting part N includes a long and thin LG bundle.

Here, consider the case where a bending load is applied beyond the tolerance in the region of the light transmitting part M and the light transmitting section composed of the transmitting part M has been broken. In this case, the replacement of the light transmitting section is required, and the light transmitting section of FIG. 16B, not only for the light transmitting part M which has been broken but also for the light transmitting part N which is not broken, must be replaced. In contrast to this, the light transmitting section shown in FIG. 16C requires only the light transmitting part M constituting the light transmitting section to be replaced, and excels in maintenance.

Also, if a condensing optical system, not shown, for concentrating the light from the light transmitting part M on the side of the light transmitting part N is provided between the light transmitters composed of the light transmitting parts M and N, the transition efficiency of light at the dividing place between the light transmitters can be improved. As such, more favorable light transmitters of the TV observation system for endoscopes can be realized.

The light transmitters shown in FIG. 16D are an example where an amount of light that is enough for observations can be secured, even when each of the light transmitting parts M and N is constructed with the LG bundle. The LG bundle constituting the light transmitting part M is adapted to transmit the light from the light source as copiously as possible to the arbitrary point P, and hence the fiber elements are bundled to be as thick as possible. The LG bundle constituting the light transmitting part N, on the other hand, is such that in response to the request for a reduction in diameter of the distal end o the endoscope, the fiber elements are configured to decrease in number and lengthen as compared with those of the LG bundle of the light transmitting part M (hereinafter, the LG bundles constituting the light transmitting parts M and N are simply referred to as an LG bundle a1 and an LG bundle b1, respectively). Thus, the relation between an area $\Phi 3$ of the exit end of the LG bundle a1 and an area $\Phi 4$ of the entrance end of the LB bundle b1 becomes $$\Phi 3 > \Phi 4 \quad (3)$$

and when the light transmitted by the LG bundle a1 is rendered incident on the LG bundle b1, a great loss of the amount of light is caused. Provision for this is made by placing a condensing optical system 45 between the LG bundles a1 and b1 so that the light transmitted by the LG bundle a1 is effectively incident on the LG bundle b1. The light collected by the condensing optical system 45 enters the entrance end of the LG bundle b1, holding a large angle of incidence.

In FIG. 17, consider now the case where a ray of the largest angle of emergence, of light emerging from the exit end of the LG bundle a1, is focused by the condensing optical system 45 to enter the entrance end of the LG bundle b1. In this case, the relation between an angle of emergence $\theta 1$ of the ray from the LG bundle a1 and an angle of incidence $\theta 2$ of the ray on the LG bundle b1 is expressed, by the function of the condensing optical system 45, as $$\theta 1 < \theta 2 \quad (4)$$

In order that this ray is rendered incident on the entrance end by the LG bundle b1 and transmitted to the distal end of the endoscope, an angular aperture NA2 of the LG bundle b1 requires at least the magnitude of the angle of incidence $\theta 2$. For an angular aperture NA1 of the LG bundle a1, by contrast, the magnitude of the angle of incidence $\theta 1$ is satisfactory. Thus, in order to suppress the loss of the amount of light caused when the ray is transmitted to the distal end of the endoscope, it is desirable that the angular apertures NA1 and NA2 at least satisfy the relation:

$$NA1 < NA2 \quad (5)$$

The angular aperture NA1 of the LG bundle a1 may be designed to equalize the angular aperture NA2 of the LG bundle b1. In this case, in view of Eq. (4) given by the function of the condensing optical system 45 situated between the LG bundles a1 and b1, it is necessary to determine the converging angle of the light source optical system in which the light from the light source is concentrated in the LG bundle a1. Specifically, the condensing optical system 45 situated between the LG bundles a1 and b1 is constructed so that the angle of incidence $\theta 2$ of the ray on the LG bundle b1 becomes nearly equal to the angular aperture NA2 of the LG bundle b1, while the light source optical system is designed so that rays having converging angles within the angle of incidence $\theta 1$ account for at least $\frac{2}{3}$ of the angular distribution of rays collected by this optical system.

Thus, in view of the relationship between the converging angle of the light source optical system and the angular aperture of the light transmitter, an arrangement ranging from the light source to the distal end of the endoscope is regarded as one connecting system to suppress the loss of the amount of light. In this way, it becomes possible to construct the illumination system for providing the amount and distribution of illumination light sufficient for observations. It is, therefore, necessary only that even when each of the light transmitters M and N is constructed with the LG bundle, the angular aperture NA1 of the LG bundle a1 and the angular aperture NA2 of the LG bundle b1 is set to satisfy the relation:

$$NA1 \leq NA2 \quad (6)$$

Also if portions close to the exit and entrance ends of the LG bundles a1 and b1 are fused into a single fiber form so that a core portion accounts for at least 80% of each of the exit and entrance ends, the incidence efficiency of light at the entrance end can be further improved.

What follows is a description of an example where the area rate of the core portion to the entrance end of the LG bundle at is 80% or more and the incidence and transmission efficiencies of light is improved.

The fiber elements used for the LG bundle of an ordinary endoscope are in the range of 0.02 to 0.05 mm diameter. For the fiber elements with a fiber diameter of 0.03 mm, as an example, cores are between 0.025 and 0.028 mm in diameter, and accounts for about 69-87%. Where these fiber elements are made for the LG bundle, however, the ratio of the cores to the entrance end of the LG bundle reduces to 50-70%. This is because the ratio of portions excluding the cores, namely a cladding and space between the fiber elements, to the entrance end is higher. The light incident on the LG bundle is totally reflected repeatedly by the boundary between each core and the cladding and is transmitted to the exit end of the LG bundle. Since the light is scattered and absorbed as the total reflection is repeated, and the amount of light is reduced, it is desirable to construct the LG bundle such that the number of times of total reflection is minimized. In the fifth embodiment, therefore, the core diameters of the fiber elements are set to 0.1 mm or more to enlarge the entire core area, and the fiber elements with a higher core ratio than the conventional fiber elements are processed and used as the LG bundle a1. In this case, the core ratio of the fiber elements can be increased to at least 92%, and the ratio of the cores to the entrance end of the LG bundle can also be increased to at least 80%. Moreover, by enlarging the core diameters, the number of times of total reflection during light transmission can be considerably reduced as compared with the conventional LG bundle.

In this way, for the light transmitting part to which a very large bending load is not applied as in the LG bundle a1 and which can be shaped into a thin and long form, the LG bundle in which the core diameters of the fiber elements are set to at least 0.1 mm is used, and thereby it is possible to construct an illumination system for endoscopes in which the incidence and transmission efficiencies of light are improved as compared with the conventional LG bundle.

For example, in an endoscope used for the purpose of inspecting the inner wall of a thick and long pipe, such as sewer piping, or searching out persons caught and enclosed in spaces under rubble produced by a disaster, a reduction in diameter of the distal end of the endoscope is not required, and it is rather necessary that the light transmitting section ranging from the entrance end to the exit end is shaped into a relatively thick and long form, and a large amount of light is transmitted to the longest possible distance. In this case, the light transmitting section need not be divided into two or more and it is only necessary that the LG bundle with a core diameter of at least 0.1 mm mentioned above is used as it is. Where the LG bundle is lengthened, it is desirable that the LG bundle is constructed with the fiber elements which have a transmission loss property of 50 dB/km or less.

Where a 10-m long LG bundle possessing this characteristic is used for light transmission, very rich illumination can be realized compared with the illumination of the conventional endoscope of this type that approximately 90% of the amount of light incident on the LG bundle can be received on the exit side.

Sixth Embodiment

This embodiment, as shown in FIG. 18, is equipped with the illumination system for endoscopes in which the endoscope body 1 and a light guide cable 47 can be separated, and when observations are made, the light guide cable 47 is connected with a connection 48 of the endoscope body 1 and the light from the light source is transmitted to the distal end of the endoscope for illumination. Further, the system of the sixth embodiment is the illumination system for endoscopes in which a small-sized light source device is mounted directly to the connection 48, without using the light guide cable 47, and the light is supplied to the distal end of the endoscope for illumination, so that, by improving the light transmitting section placed in the endoscope body 1, the distal end of the endoscope is rendered smaller in diameter than that of the conventional endoscope of this type and more copious illumination can be performed.

An endoscope is structurally separated into two parts, one that it is desirable to make the diameters of the distal end of the endoscope and other parts as small as possible and the other that it is necessary to construct the endoscope which affords ease of holding and operation by priority and has a sufficient size. Specifically, the dividing point P is taken close to the boundary between the former and the latter so that the endoscope body 1 is separated into the light transmitting part N provided in the former and the light transmitting part M in the latter. Also, the connection with the light guide cable 47 is provided on the side of the light transmitting part M.

The light transmitting section of the conventional endoscope, as already shown in FIG. 13, is constructed with a single LG bundle, and hence if the number of fiber elements of the LG bundle is decreased in accordance with a tendency to the smaller diameter of the distal end of the endoscope, the amount of transmissible light will be materially reduced.

FIG. 19A shows a condensing optical system 52 including a collector lens 53 and a reflecting mirror 54, of the connection adopted when a single fiber 51 having no flexibility is used. FIG. 19B shows a condensing optical system 56 including the collector lens 53, of the connection adopted when a single fiber 55 having flexibility is used.

In the sixth embodiment, the light transmitting section shown in FIG. 20A is divided at the dividing point P into the light transmitting parts M and N, which are each constructed with a single fiber. The single fiber constituting the light transmitting part M (which is hereinafter referred to as a single fiber a2) is configured so that an area Φ5 of the entrance end situated opposite to the condensing optical system, such as that shown in FIG. 19A or 19B, provided at the connection of the light guide cable is maximized, and is such that the sectional area normal to the optical axis is reduced progressively in going from the entrance end to the dividing point P, and the single fiber is shaped into a practical taper form.

On the other hand, the single fiber constituting the light transmitting part N (which is hereinafter referred to as a single fiber b2) is configured so that an area Φ7 of the entrance end is larger than an area Φ6 of the exit end of the single fiber a2, and part of the single fiber b2 is shaped into a practical taper form so that the area Φ7 approaches an area Φ8 of the exit end of the single fiber b2 progressively toward the distal end of the endoscope. Furthermore, an angular aperture NA4 of the single fiber b2 is set to become larger than an angular aperture NA3 of the single fiber a2. By constructing the light transmitting section in this way, the incidence efficiencies of light at the light guide connection and the dividing point of the light transmitting section are improved, and an angle of distribution of the light emerging from the exit end of the single fiber b2 can be increased.

The light transmitting section shown in FIG. 20B is such that the light transmitting part N of FIG. 20A is constructed with the LG bundle. Even when the light transmitting section is designed in this way, illumination light of sufficient brightness can be supplied without obstructing observations. In addition, the flexibility of the portion such as the distal end of the endoscope inserted in the observation part can be improved.

In order that the condensing optical system is placed at the dividing point P between the light transmitting parts M and N to improve the condensation efficiency of light at the entrance end of the LG bundle, it is desirable that an angular aperture NA5 of the single fiber constituting the light transmitting part M and an angular aperture NA6 of the LG bundle constituting the light transmitting part N satisfy the relation:

$$NA5 < NA6 \tag{7}$$

By satisfying Eq. (7), it becomes possible to improve the incidence efficiency of light at the entrance end of the LG bundle, and a more favorable illumination system can be provided.

The light transmitting section shown in FIG. 20C is such that the light transmitting part N of FIG. 20A is constructed with the LG bundle, which is fused with the single fiber constituting the light transmitting part M. The light transmitting parts M and N are fused and connected, and thereby a loss of light at the connection can be essentially prevented. Moreover, since the light transmitting part N is constructed with the LG bundle, the flexibility of the portion such as the distal end of the endoscope inserted in the observation part can be improved.

Seventh Embodiment

This embodiment, as illustrated in FIG. 21A, is equipped with the illumination system for endoscopes in which the light guide cable 47 can be separated from a rigid endoscope body "1" provided with a lengthened and non-flexible insertion part 1", and when observations are made, the light guide cable 47 is connected with the connection 48 of the rigid endoscope body 1" and the light from the light source is transmitted to the rigid endoscope body 1" for illumination. For the conventional system of this type, there is, for example, a cystoscope which is inserted in a fine urethra to observe and treat the prostate gland and the urinary bladder. The cystoscope has the lengthened and non-flexible insertion part 1" for making an insertion in the fine urethra, and is considered so that the entire system is constructed from very lightweight and compact design, including a rigid portion subsequent to the insertion part 1", to thereby improve an observer's operability and reduce a patient's load as far as possible. The interior of the urinary bladder spreads into a spherical shape, which seems as if the insertion part 1" of the endoscope would be inserted in the air hole of a rubber ball to observe the inside of the ball. Thus, in order to copiously illuminate the observation field including its periphery, a sufficient amount of light becomes a necessity. In the conventional illumination system for endoscopes of this type, however, since the light transmitting section is separated into the endoscope body and the light guide cable and uses the LG bundle in which the fiber elements are in the range of 0.02 to 0.05 mm diameter, such as that described in the fifth embodiment, the efficiency for transmitting the light from the light source to the distal end of the endoscope is impaired, and a sufficient amount of light for observations is not derived. To meet this problem, the number of fiber elements is increased which constitute the LG bundle situated on the side of the light guide cable which can be shaped into a relatively thick and long form, and the numerical aperture of the fiber elements constituting the LG bundle on the endoscope body side is set to be larger than that of the fiber elements on the light guide side. By doing so, the transmission efficiency of light of the light transmitting section is raised, and a sufficient amount of light for observations can be ensured. In this case, however, that the light guide cable is shaped into the thick and long form causes the observer's operability to be considerably deteriorated, which is unfavorable for the endoscope system such as the cystoscope requiring the lightweight and compact design. The seventh embodiment thus provides the observation system for endoscopes in which the above problem can be solved to richly illuminate the observation field, and the lightweight and compact design is achieved.

The light transmitting part, shown in FIG. 21B, on the side of the light guide cable uses a single fiber instead of the conventional LG bundle. By doing so, the transmission efficiency of light is much improved, and at the same time, reductions in diameter and weight of the light guide cable itself are realized. Thus, as already explained in other embodiments, the incidence efficiency of light at the entrance end and the efficiency for transmitting light to the exit end are enhanced by constructing the light transmitter with the single fiber, so that the amount of light secured by the conventional light guide cable, as the result that the number of fiber elements of the LG bundle is increased to enlarge the diameter, is obtained with the diameter reduced.

If the light transmitting part on the side of the endoscope body, as in the conventional endoscope, uses the LG bundle such that an angular aperture NA7 of a light transmitter A1 on the side of the light guide cable and an angular aperture NA8 of a light transmitter B1 on the side of the endoscope body satisfy the relation:

$$NA7 \leqq NA8 \tag{8}$$

the amount and distribution of light sufficient for observations can be ensured. At this time, in view of the fact that the endoscope used in the observation system of the seventh embodiment is the rigid endoscope provided with the lengthened and non-flexible inserting portion, if, as shown in the fifth embodiment, the LG bundle in which the core diameter of the fiber elements is set to 0.1 mm or more is used, the transmission efficiency of light on the side of the endoscope body will be further enhanced and the observation field can be richly illuminated, including its periphery. In this case, close to the connection with the light guide cable provided in the endoscope which is easy to ensure space required for placing the LG bundle, the LG bundle, as shown in the figure, can be located as it is. In contrast to this, at the place where space sufficient for locating the LG bundle, as it is, cannot be secured as in the lengthened insertion part 1', the LG bundle is separated in accordance with individual fiber elements so that an extremely limited space of the observation part is effectively utilized, and thereby copious illumination can be realized, although the diameter of the insertion part is smaller. The endoscope system such as the cystoscope must be very light in weight, and thus it is favorable that optical plastic which is lower in specific gravity than glass is used as the materials of the single fiber and the fiber elements employed for the light transmitting section of the endoscope system.

FIG. 21C shows the light transmitting section of the illumination system for endoscopes which is favorable for a further reduction in diameter and compactness of the endoscope system. The single fiber is used for the light transmitter A1 situated on the light guide side, and is shaped into a taper form so that the sectional area of the entrance end reduces progressively in going to the exit end, thereby improving the incidence efficiency of light. For the light transmitter B1 on the endoscope body side, the single fiber satisfying Eq. (8) is placed. It is for this reason that when the diameter of the insertion part of the endoscope is as small as 1.5 mm or less, the use of the single fiber, rather than the LG bundle as the light transmitter, brings about the advantages of enabling the light to be transmitted to the distal end of the endoscope without loss and of facilitating the assembly of the insertion part.

Thus, in a lightweight and compact endoscope system having the insertion part of extremely small diameter, when the light transmitting section of the endoscope shown in FIG. 21C is employed, the observation field can be richly illuminated and the endoscope system which excels in assembly can be realized.

Also, it is favorable that the connection between the light guide cable and the endoscope body is provided with the condensing optical system, although not shown in FIGS. 21B and 21C, to transmit the light from the light guide cable to the endoscope body without loss so that the transmission efficiency of light is further improved.

Eighth Embodiment

In recent years, endoscopic surgery has come to be generally performed. This surgery is such that, as represented by laparoscopic surgery, the endoscope and an operation tool are merely inserted into the cavity of the human body, without cutting out its somatic layer, and thereby observations are made through the endoscope so that the tool is manipulated to cut off organs. In such surgery, the surroundings of an operating table on which a patient lies down are taken as a sanitary region, and thus it is not allowed that things which are not sterilized, for example, by a disinfectant are brought into the sanitary region. Further, it is also not allowed that such obstacles that the behavior of a surgeon who performs the operation is restricted and his work efficiency is considerably impaired are placed in the surroundings of the operating table. It is thus impossible to take means that a movable rack mounting the light source device, the TV processor, and the monitor is placed close to the surgeon and the patient, as in a diagnosis for which the conventional endoscope is used.

For the endoscopic observation in the above operation, rich illumination of a wide space in the human body is indispensable, and it becomes necessary to construct the illumination system for endoscopes which is capable of transmitting a large amount of light from the light source to the distal end of the endoscope. Furthermore, the endoscopic observation sometimes requires several kinds of endoscopes to be used at the same time in such a way that one endoscope is used to observe the interior of the human body over a wide range and hold the positional relation between the operation tool inserted in the human body and an affected part and another endoscope is used to magnify the affected part to observe its detail during treatment. The eighth embodiment provides the illumination system for endoscopes which is capable of accommodating such conditions.

The system of the eighth embodiment, as depicted in FIG. 22, is constructed so that light from a light source 61 situated at a place away from the sanitary region of the surroundings of the operating table is transmitted to the neighborhood of the operating table by the light guide cable 47, and is optically transferred through a connection 62 to a plurality of light guide cables 63.

Since the light guide cable 47 conducts the light from the light source 61 to the connection 62 located close to the operating table, the entire length of at least 10 m becomes a necessity. The light guide cable 47 and the connection 62 must be placed so that the behavior of the surgeon who performs the operation is not obstructed, and hence, for example, a flexible arm of suspension type is provided in a space above the operating table so that the connection is mounted at the top of the arm and the light guide cable 47 is incorporated inside the arm. It is thus necessary for the light guide cable 47 to have some degree of flexibility.

In order that, as mentioned above, requirements for the light guide cable 47 to be fulfilled and a great deal of light can be transmitted from the light source 61 to the connection 62, the eighth embodiment employs the following two kinds of light transmitters. One of them is such that the LG bundle is used which has a core diameter of at least 0.1 mm and a transmission loss characteristic of up to 50 dB/km with respect to the fiber elements such as those shown in the fifth embodiment, and thereby a large amount of light is brought to the connection 62 located at a distance of 10 m from the light source 61 and the light guide cable 47 can be designed to have flexibility.

Since the LG bundle having the foregoing features enables the core ratio at the entrance end to be raised to 80% or more, a great deal of light can be rendered incident on the LG bundle, and even when the light is transmitted over a distance of 10 m, a transmission loss can be suppressed to about 10% and thus the light incident on the LG bundle can be taken out, without little loss, on the exit end thereof.

The other is such that a liquid light guide is employed in which a flexible tube is filled with a transparent liquid which is higher in refractive index than the tube and transparent window members are mounted to openings at the ends of the tube, and thereby the requirements for the light guide cable 47 can be fulfilled.

Where the liquid light guide, which may be thought of as the single fiber, has the same outside diameter as the LG bundle, a much larger amount of light than in the LG bundle can be rendered incident, and the number of times of total reflection during transmission can be reduced to suppress a loss of the amount of light. Moreover, because the transparent liquid which is light-transmissive is enclosed in the flexible tube, the liquid light guide can sufficiently withstand the bending load to some extent.

Even where the liquid light guide is used in this way, the amount of light which is equal to, or greater than, the case of the LG bundle can be transmitted, so that each of the plurality of endoscopes 63 connected through the connection 62 with the light guide cable 47 can supply light sufficient for rich illumination.

The transparent liquid enclosed in the liquid light guide may have the property of absorbing light of a particular wavelength, such as an infrared ray, and may be degraded by the influence of the light absorbed into the liquid to materially impair the transmission performance of light. In this case, the light source optical system is provided with means for removing the light of absorbed wavelength to prevent the deterioration of the performance so that the light transmitting section with good durability is realized.

In FIG. 23A, a great deal of light transmitted by the light guide cable 47 is split up and supplied to the plurality of light guide cables 63 by a connecting optical system 70, which includes a total reflection mirror 71, a path splitting mirror 72, a total reflection mirror 73, and condensing optical systems 74 and 75.

The light emerging from the light guide cable 47, after being totally reflected by the total reflection mirror 71, is broken, by the path splitting mirror 72, into optical paths $0_1$ and $0_2$, which are introduced to the entrance ends of the plurality of (two) light guide cables 63 by the condensing optical systems 74 and 75, respectively. The path splitting mirror 72, as shown in FIG. 23B, is such that at least three regions composed of a total reflection mirror 72a, a semi-transmission mirror 72b, and a total transmission window 72c are selectively constructed. The path splitting mirror 72, for example, has the mechanism that where one of the plurality of light guide cables 63 is connected only to the optical path $0_1$, the total reflection mirror 72a is selected automatically. In addition, where the plurality of light guide cables 63 are not entirely connected to the connecting optical system 70, provision is made for closing a shutter located on the side of the light source optical system to shut off the supply of light to the light guide cable 47.

The path splitting mirror 72 may be constructed so that the ratio between the amounts of light for transmission and reflection can be selected in more detail. Further, a stop for adjusting the amount of light is disposed in the optical path so that the supply of light to the plurality of light guide cables 63 can be controlled. Still further, if a beam re-forming optical system is interposed between the light guide cable 47 and the path splitting optical system to re-form the spread of a beam of light, a loss of the amount of light at the connecting optical system 70 can be compactly designed.

As stated above, the light transmitter most suitable for transmitting the light over a long distance is used to construct the light guide cable 47, and further the use of the connecting optical system 70 makes it possible to supply the light to the plurality of light guide cables 63. In this way, the illumination system for endoscopes which is capable of accommodating endoscopic surgery can be provided.

Ninth Embodiment

The illumination system for endoscopes comprises a light source emitting light for illuminating an object to be observed, a light transmitting section for transmitting the light from the light source to the distal end of the endoscope, and an illuminating optical system for radiating the light transmitted by the light transmitting section toward the object. In this illumination system for endoscopes, the technique has been shown that as means for bringing about the amount of light sufficient for richly illuminating the object at the distal end of the endoscope, the light transmitters constituting the light transmitting section, most suitable for structures of individual parts of the endoscope, are selectively used and thereby the transmission efficiency of light is generally enhanced. In the ninth embodiment provides a technique for securing a desired brightness by using another means.

The light source optical system for endoscopes includes a light emitting section for emitting light and a condensing optical system for concentrating the light from the light emitting section onto the entrance end of the light transmitting section of the endoscope. In the condensing optical system, namely the optical system for projecting an image of the light emitting section on the entrance end, the diameter of a beam of light at the entrance end depends on its projection magnification. The angle of incidence of light on the entrance end is governed by the focal length of the condensing optical system.

Thus, in the ninth embodiment, the light source optical system for endoscopes is constructed so that, in view of the numerical aperture of the light transmitter with the entrance end and the diameter of the entrance end, light from the light source optical system is most efficiently incident on the light transmitter. In this way, a desired brightness can be obtained at the distal end of the endoscope.

The light source optical system in the ninth embodiment, as depicted in FIG. 24, comprises a light emitting section 80, a condensing optical system 81, a reflection mirror 82, and a light transmitter 83.

Here, reference is made to the dimensions of the light emitting section 80 of the light source optical system for endoscopes in the ninth embodiment. In FIG. 24, with respect to the condensing optical system 81 which projects the image of the light emitting section 80 on the entrance end of the light transmitter 83 at an equimagnification, the relation between an outer diameter D1 of the entrance end and a dimension L of the light emitting section 80 of the light source is defined by $$1.0 < D1/L < 1.5 \tag{9}$$

By setting the projection magnification of the condensing optical system to 1×, the image of the light emitting section 80 can be projected on the entrance end in such a way that aberrations yielded by the condensing optical system 81 is reduced to a minimum. Consequently, unevenness of luminance is not caused with respect to the cross section of the light beam cut normal to the optical axis, and as such the light can be rendered incident on the entrance end at the highest efficiency. Additionally, the relation between the outer diameter D1 of the entrance end and the dimension L of the light emitting section 80 is defined by Eq. (9), and thereby nearly all the light concentrated by the condensing optical system 81 can be rendered incident on the entrance end. Where the lower limit of Eq. (9) is passed, all the light concentrated by the condensing optical system 81 cannot be rendered incident on the entrance end. Beyond the upper limit, the light is incident on only a part of the entrance end, unevenness of intensity distribution is caused by emergent light on the exit end of the light transmitter with the entrance end, which is unfavorable. Since the condensing optical system 81 can be structurally divided into front and rear lens units and constitutes the optical system of equimagnification, the front and rear lens units have the same focal length f. Thus, for the condensing optical system 81 of the ninth embodiment, the relation between the focal length f and an outer diameter D2 of each lens is defined by $$0.575 \leq |f/D2| \leq 1.0 \tag{10}$$

when the focal length f decreases as the lower limit of Eq. (10) is passed, the radius of curvature of the lens surface is reduced, with a resulting deterioration in workability of the lens. On the other hand, where the focal length f increases as the upper limit is exceeded, a solid angle decreases which is subtended at the light emitting section by a lens surface closest to the light emitting section 80, and the light from the light emitting section 80 ceases to be completely captured by the condensing optical system 81. In order to avoid this difficulty, the outer diameter of the lens must be enlarged, and when a light source unit is constructed, a space occupied by the condensing optical system 81 is increased, which is unfavorable.

In Eq. (10), the term |f/D2| indicates the absolute value of the F-number of the rear lens unit. Calling θ the angle of incidence of light on the entrance end of the light transmitter, the limit of the angle of incidence θ is determined by $$0.5 \leq \sin\theta \leq 0.87 \tag{11}$$

This is the limit of the angle of incidence at which the light source optical system of the ninth embodiment is capable of making the light emitted from the light emitting section 80 incident at the incidence efficiency favorable for the light transmitter. For example, in the endoscope in which the LG bundle having an outer diameter of 1.0 mm and a numerical aperture NA of 0.6 at the entrance end is used as the light transmitter, when the condensing optical system is constructed by combining lens units, each having the focal length f such that the angle of incidence, sin θ, becomes 0.6, and further the light source optical system is constructed by using the light source composed of the light emitting section 50 with the dimension L=1.0 mm, the illumination system for endoscopes can be constructed which provides brightness sufficient for illumination light of the endoscope.

Where the illumination system for endoscopes is constructed using the light source optical system for endoscopes of the ninth embodiment, Eq. (11) can be rewritten in such a manner that it shows that the numerical aperture NA of the light transmitter constituting the light transmitting section of the endoscope need be determined by $$0.5 \leq NA \leq 0.87 \qquad (12)$$

Also, where the light source is of electric discharge type, the dimension L of the light emitting section 80, as shown in FIG. 25A, may be represented in terms of the distance between electrodes EL. Alternatively, where it is of filament type, as shown in FIG. 25B, the dimension L can be designated by the diameter of a circle Q, as its center at an optical axis O, circumscribed about a filament of cross section cut normal to the optical axis O.

If the light source optical system for endoscopes of the ninth embodiment is used in combination with the light transmitter of the endoscope shown in each of the fifth to eighth embodiments, it is needless to say that the illumination system for endoscopes which brings about more copious illumination light can be constructed.

What is claimed is:

1. A TV observation system for an endoscope, comprising:
    an endoscope;
    a TV camera; and
    a light source,
    wherein the endoscope has an insertion part having a thin and long shape, a holding part continuously extending from a proximal end of the insertion part, an eyepiece section formed on the holding part, a light guide that introduces illumination to a distal end of the insertion part, a light source connecting section formed on the holding part to achieve removable connection of the light source,
    wherein the TV camera has an image pickup element and said TV camera is optically connected to the eyepiece section of the endoscope to receive an optical image through said eyepiece section, and
    wherein the light source comprises a plurality of LEDs, said light source is removably connected to the light source connecting section, and the light source supplies illumination light to the light guide of the endoscope.

2. A TV observation system for an endoscope according to claim 1, wherein the light source further comprises an optical element that compounds light emitted from the plurality of LEDs.

3. A TV observation system for an endoscope according to claim 1, wherein the TV camera further comprises a battery that supplies an electric current to the light source.

4. A TV observation system for an endoscope according to claim 1, wherein the light source further comprises a control mechanism that controls electric currents applied to the plurality of LEDs, so that amounts of light emission of the LEDs are set in a desired ratio.

5. A TV observation system for an endoscope according to claim 1, wherein the light source is configured to sequentially emit a light of at least three colors, and comprises a LED that emits red light, a LED that emits green light, and a LED that emits blue light.

6. A TV observation system for an endoscope according to claim 2, wherein the optical element is a prism that has a cubic shape made of two right-angled prisms cemented together at fitting surfaces, and the fitting surfaces are processed with a bandpass coating, which has a characteristic to transmit rays with predetermined wavelengths and to reflect remaining rays.

7. A TV observation system for an endoscope according to claim 2, wherein the optical element is a planar-plate optical member having a fine pattern of grooves engraved on a surface thereof, and compounds light emitted from the plurality of LEDs using a diffraction effect.

8. A TV observation system for an endoscope, comprising:
    an endoscope;
    a TV camera; and
    a light source,
    wherein the endoscope has an insertion part having a thin and long shape, a holding part continuously extending from a proximal end of the insertion part, an eyepiece section formed on the holding part, a light guide that introduces illumination light to a distal end of the insertion part, a light source connecting section formed on the holding part to achieve removable connection of the light source,
    wherein the TV camera has an image pickup element and said TV camera is optically connected to the eyepiece section of the endoscope to receive an optical image through said eyepiece section, and
    wherein the light source comprises a plurality of LEDs, and said light source is integrally constructed with the TV camera.

9. A TV observation system for an endoscope according to claim 8, wherein the TV camera further comprises a battery that supplies an electric current to the light source.

10. A TV observation system for an endoscope according to claim 8, wherein the light source further comprises a control mechanism that controls electric currents applied to the plurality of LEDs, so that amounts of light emission of the LEDs are set in a desired ratio.

11. A TV observation system for an endoscope according to claim 8, wherein the light source is configured to sequentially emit light of at least three colors, and comprises a LED that emits red light, a LED that emits green light, and a LED that emits blue light.

12. A TV observation system for an endoscope according to claim 8, further comprising an optical element that compounds light emitted from the plurality of LEDs.

13. A TV observation system for an endoscope according to claim 12, wherein the optical element is a prism that has a cubic shape made of two right-angled prisms cemented together at fitting surfaces, and the fitting surfaces are processed with a bandpass coating, which has a characteristic to transmit rays with predetermined wavelengths and to reflect remaining rays.

14. A TV observation system for an endoscope according to claim 12, wherein the optical element is a planar-plate optical member having a fine pattern of grooves engraved on a surface thereof, and compounds light emitted from the plurality of LEDs using a diffraction effect.

15. A light source mounted on an endoscope that comprises an insertion part having a thin and long shape, a holding part continuously extending from a proximal end of the insertion part, an eyepiece section formed on the holding part and providing an optical connector to attach a TV camera to receive an optical image therethrough, a light guide that introduces illumination light to a distal end of the insertion part, a light source connecting section formed on the holding part to achieve removable connection of the light source,
    the light source comprising a plurality of LEDs and supplies illumination light to the light guide of the endoscope.

16. A light source according to claim 15, further comprising an optical element that compounds light emitted from the plurality of LEDs.

17. A light source according to claim 15, further comprising a control mechanism that controls electric currently applied to the plurality of LEDs, so that amounts of light emission of the LEDs are set in a desired ratio.

18. A light source according to claim 16, wherein the optical element is a prism that has a cubic shape made of two right angled prisms cemented together at fitting surfaces, and the fitting surfaces are processed with a bandpass coating, which has a characteristic to transmit rays with predetermined wavelengths and to reflect remaining rays.

19. A light source according to claim 16, wherein the optical element is a planar-plate optical member having a fine pattern of grooves engraved on a surface thereof, and compounds light emitted from the plurality of LEDs using a diffraction effect.

* * * * *